United States Patent [19]

Maeda

[11] Patent Number: 5,400,135

[45] Date of Patent: Mar. 21, 1995

[54] AUTOMATIC DEFECT INSPECTION APPARATUS FOR COLOR FILTER

[75] Inventor: Ichiro Maeda, Tokyo, Japan

[73] Assignee: Nikon Corporation, Tokyo, Japan

[21] Appl. No.: 229,014

[22] Filed: Apr. 18, 1994

[30] Foreign Application Priority Data

Jun. 8, 1993 [JP] Japan ................... 5-163904

[51] Int. Cl.$^6$ ............................................. G01N 21/88
[52] U.S. Cl. .................... 356/237; 356/394; 356/398
[58] Field of Search ............... 356/237, 394, 398, 416, 356/419; 359/891

[56] References Cited

FOREIGN PATENT DOCUMENTS

| 1-9402 | 1/1989 | Japan | 359/891 |
|---|---|---|---|
| 3-115945 | 5/1991 | Japan | 356/416 |
| 5-99787 | 4/1993 | Japan | 356/416 |
| 6-58839 | 3/1994 | Japan . | |

*Primary Examiner*—F. L. Evans
*Attorney, Agent, or Firm*—Shapiro and Shapiro

[57] ABSTRACT

An automatic defect inspection apparatus for a color filter includes a light source for radiating light onto a color filter having a spatially periodical repetitive structure of red, green, and blue, a detector for detecting light from the color filter, and a processor for executing arithmetic processing of the output signal from the detector. In the apparatus, the detector is arranged to detect the light radiated form the light source and transmitted through the color filter, and a diaphragm for limiting the area of the transmitted light incident on the detector in association with an integer multiple of the spatially periodical repetitive structure of red, green, and blue is arranged.

17 Claims, 15 Drawing Sheets

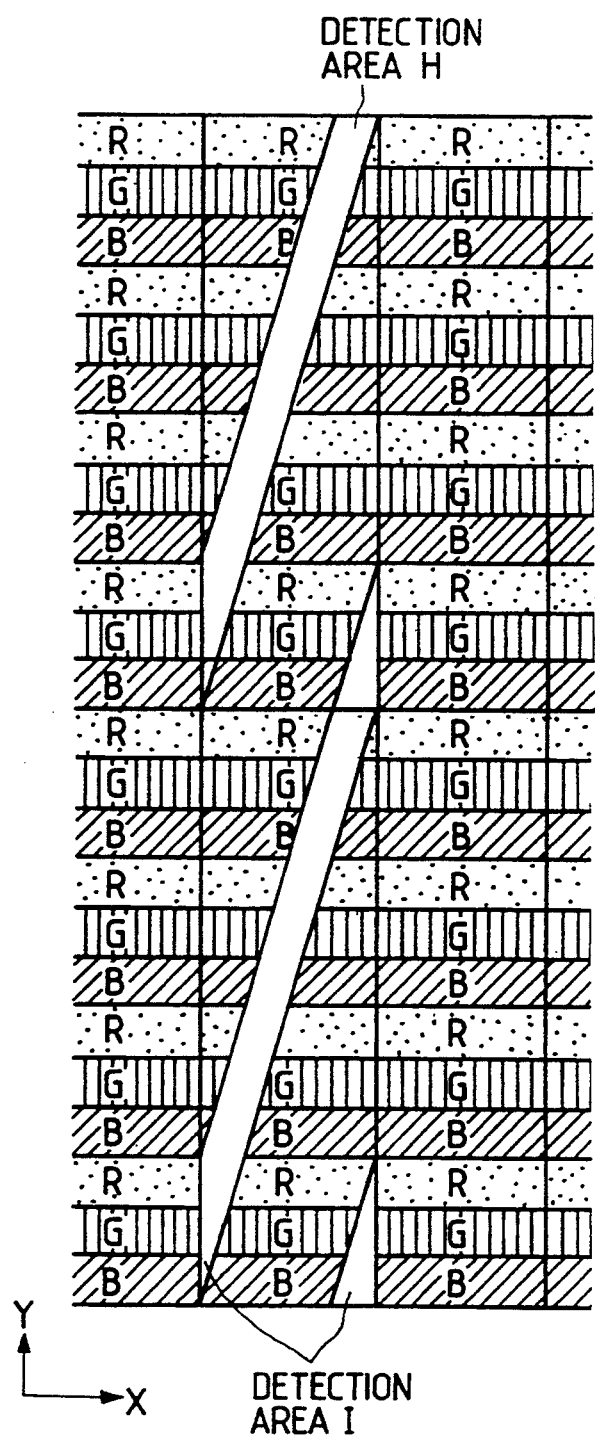

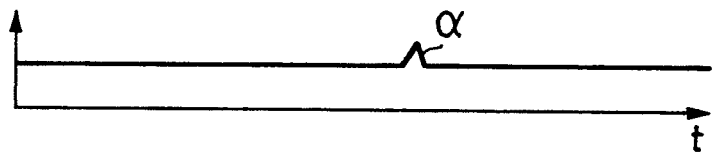
FIG. 20A
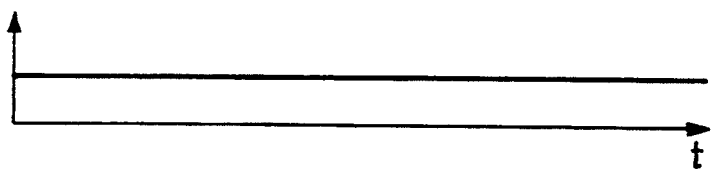
FIG. 20B
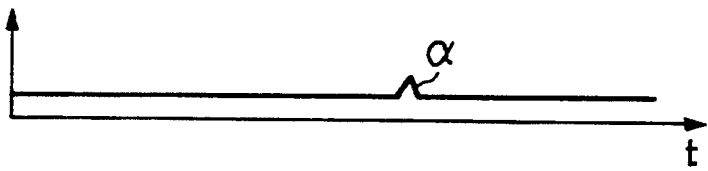
FIG. 20C
FIG. 21
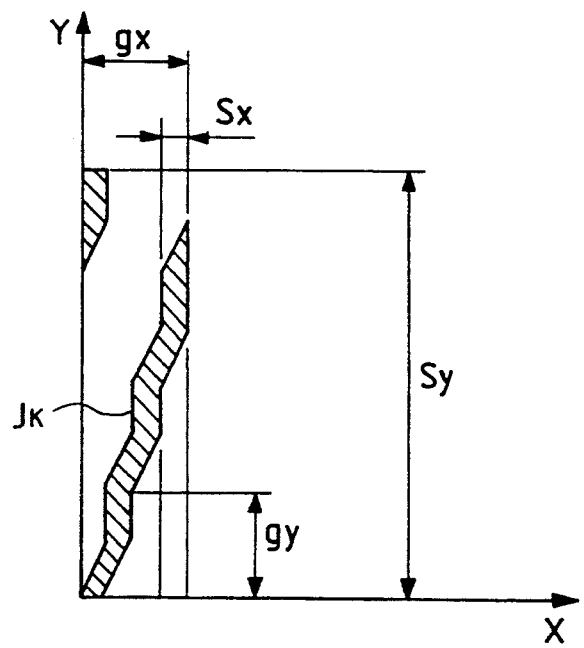

AUTOMATIC DEFECT INSPECTION APPARATUS FOR COLOR FILTER

BACKGROUND OF THE INVENTION

1. Field of the Invention

The present invention relates to an automatic defect inspection apparatus for a color filter and, more particularly, to an automatic defect inspection apparatus for a color filter, which is suitably used in automatic defect detection/inspection of a color filter which is, in turn, used in, e.g., a liquid crystal display device and has a spatially periodical repetitive structure of red, green, and blue.

2. Related Background Art

In conventional defect inspection of color filters used in, e.g., a liquid crystal display device, an inspection person normally visually inspects all the filters. Since this defect inspection method depends on sensory organs of man, the defect inspection result varies depending on the physical conditions and individual differences of the inspection persons, and it is difficult to attain stable defect inspection.

Also, various methods of automatically detecting defects using machines independently of the sensory organs of man have been proposed. However, these methods are still in the process of experimentation, and are not put into practical applications.

Of automatic defect inspection apparatuses which have been proposed, an automatic defect inspection apparatus which uses a video camera comprising a line sensor such as a CCD as detection means for detecting light from a color filter is known. In this defect inspection apparatus, since too small an area corresponding to one pixel of the line sensor is used as one measurement unit, a large volume of measurement data must be subjected to arithmetic processing, and a special-purpose arithmetic device capable of performing high-speed arithmetic processing is required, resulting in a very expensive apparatus.

Furthermore, since all the conventionally proposed automatic defect inspection apparatuses for color filters have a structure for detecting patterns of defects, they have insufficient detection performance for defects with unclear edges such as unevenness, a shadowy portion, and the like which are not so serious but are present in a wide area or range.

Note that the types of defects of a color filter include a projection, white hole, white shadowy portion, color mixing, unevenness, and the like. The projection is a portion of a color filter, which projects on the color filter, and the white hole is a defect which appears white in a narrow area as if a hole were formed in the color filter. Also, the white shadowy portion is a defect which appears to be shadowy white in a relatively wide area as if the colors of the color filter were lightened, and the color mixing indicates a portion where red, green, and blue color filters are locally mixed. Furthermore, the unevenness indicates a portion which appears to be so-called "unevenness" when the color filter is observed, and is a defect which has a lower contrast and a wider area than those of the "hole". Note that other defects of the color filter include a "black hole" which is a defect observed black due to foreign matter mixed in the filter, an "unusual black line" which indicates a portion of a black line suffering from blur, which black line partitions red, green, and blur color portions, and the like.

SUMMARY OF THE INVENTION

The present invention has been made in consideration of the above situation, and has as its object to provide a practical automatic defect inspection apparatus which can automate defect detection to preclude conventional visual inspection by an inspection person, can eliminate the above-mentioned drawbacks of the conventionally proposed automatic defect inspection apparatuses, and which can detect all defects including a shadowy portion, unevenness, and the like of a color filter with low cost.

An automatic defect inspection apparatus for a color filter according to the present invention comprises a light source for radiating light onto a color filter having a spatially periodical repetitive structure of red, green, and blue, detection means for detecting light from the color filter, and processing means for executing arithmetic processing of an output signal from the detection means. In particular, in the apparatus, the detection means is arranged to detect the light radiated from the light source and transmitted through the color filter, and detection area designation means for limiting the area of transmitted light to be incident on the detection means to an integer multiple of the spatially periodic repetitive structure of red, green, and blue of the color filter is arranged.

The automatic defect inspection apparatus for a color filter according to the present invention preferably comprises a plurality of detection means and a plurality of detection area designation means, and the processing means includes an arithmetic circuit for calculating a difference between detection signals from the detection means.

Also, the length of the area of transmitted light to be incident on the detection means may be limited to an integer multiple of a period in the spatially periodical repetitive direction of red, green, and blue of the color filter, and may be limited to an area smaller than one pixel in a direction transverse to the periodical repetitive direction.

Furthermore, in the automatic defect inspection apparatus for a color filter according to the present invention, the detection area designation means preferably elongates the area of transmitted light to be incident on the detection means in the periodical repetitive direction so as to limit the area to an area equal to an area of one pixel of the color filter.

More preferably, the area of the detection area designation means is preferably slightly inclined with respect to the periodical repetitive direction when it is elongated in the periodical repetitive direction.

The automatic defect inspection apparatus for a color filter according to the present invention utilizes the regular structure of the color filter and a change in light transmittance at a defect position. More specifically, at the defect position of the color filter, phenomena such as a change in transmittance of light, generation of scattered light, and the like occur, and the present invention detects a defect by detecting the change in transmittance in these phenomena.

Since the apparatus of the present invention detects not the pattern of a defect of the color filter but the change in transmittance, the measurement unit in a single inspection can be set to be sufficiently large, and the number of data can be decreased, thus avoiding huge arithmetic processing. Furthermore, the apparatus of the present invention can detect a defect with an unclear edge such as a shadowy portion. Since the color filter has a structure in which pixels each including a set of filters corresponding to red, green, and blue are regularly aligned, and the detection area is set to be an integer multiple of the periodical repetitive structure of red, green, and blue in correspondence with this structure, a constant light amount intensity can be obtained (when the filter does not suffer from any defects) regardless of the detection position of the filter, and defect detection can be attained with reference to this value.

Light amount measurement is performed at a plurality of positions, and a difference between these measured values is calculated, thereby extracting a change in only a deformed portion corresponding to a defect. Thus, the presence and level of a defect can be clarified.

Since the detection area is limited to an integer multiple of the periodical repetitive structure of red, green, and blue of the color filter, and is limited to an area smaller than one pixel in the direction transverse to the periodical repetitive direction, a defect smaller than one pixel can be detected, and a variation in photometry value other than a defect can be reduced to decrease noise, thereby eliminating any error.

Furthermore, since the detection area is elongated in the periodical repetitive direction to have an area equal to one pixel of the color filter, the light amount measurement value can be made constant, thereby eliminating any error.

BRIEF DESCRIPTION OF THE DRAWINGS

FIG. 18 is a view showing an example of the method of designating the detection area of a mesh type color filter using the selector diaphragm shown in FIG. 17;

FIGS. 20A to 20C are waveform charts showing the output waveforms from a light receiving element and a controller in the embodiment shown in FIG. 1 obtained when the detection area is designated, as shown in FIG. 18, and detection areas A and B are slightly shifted from each other;

FIG. 21 is a view showing still another example of the selector diaphragm; and

DETAILED DESCRIPTION OF THE PREFERRED EMBODIMENTS

Figure 1:
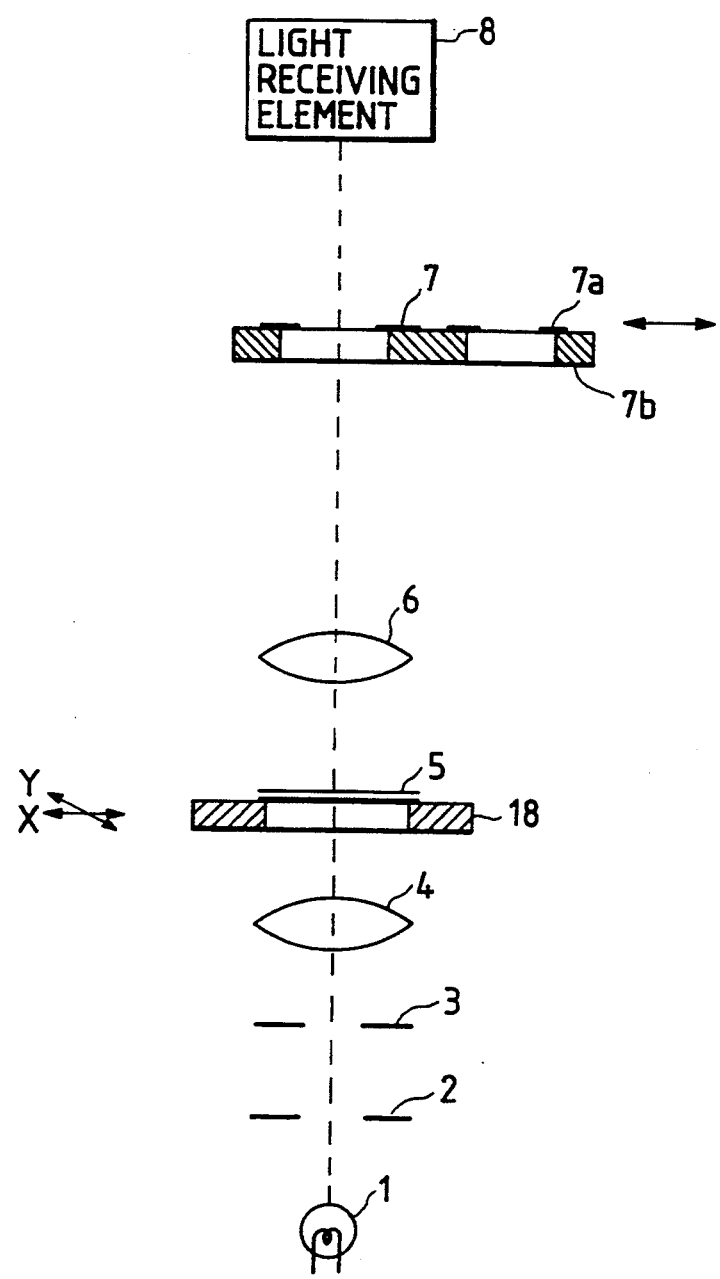
FIG. 1 is a view showing the optical arrangement according to the first embodiment of the present invention.

The preferred embodiments of the present invention will be described hereinafter with reference to the accompanying drawings.

An apparatus according to the first embodiment of the present invention will be described below with reference to FIGS. 1 and 2.

A light source 1 is an illumination light source such as a halogen lamp, a tungsten lamp, or the like. A field stop 2 is arranged in front of the light source 1. An aperture stop 3 is arranged in front of the field stop 2, and an illumination lens 4 is arranged in front of the aperture stop 3. The illumination lens 4 condenses light emitted from the light source 1 via the field stop 2 and the aperture stop 3, and illuminates a portion of a color filter 5 with the condensed light. The field stop 2 is arranged at a position conjugate with the color filter 5 with respect to the illumination lens 4, and the illumination area of the color filter 5 illuminated with the light emitted from the light source 1 is determined on the basis of the aperture pattern of the field stop 2. The aperture stop 3 adjusts the illumination light amount on the basis of the size of its aperture. The light source 1, the field stop 2, the aperture stop 3, and the illumination lens 4 constitute an illumination optical system. The color filter 5 as an object to be inspected is illuminated by this illumination optical system.

The color filter 5 is arranged on a stage 18. A through hole is formed in the stage 18 so that the color filter 5 can be illuminated with transmitted light. Also, the stage 18 is movable in a plane (X and Y directions) transverse to the optical axis. Furthermore, the stage 18 is driven by an electric motor attached thereto.

A detection means is arranged to oppose the illumination optical system in association with the color filter 5, and detects some light components transmitted through the color filter 5. The detection means comprises an objective lens 6, a selector diaphragm 7, and a light receiving element 8. The objective lens 6 forms an optical image of the color filter 5 illuminated by the illumination optical system on the selector diaphragm 7. The objective lens 6 adopts a lens with a relatively small magnification such as x1.5, x2.5, x5, or the like in correspondence with each specific application purpose. The objective lens is switched by a revolver (not shown) which is well known in the field of microscopes. The selector diaphragm 7 is attached to a rectangular plate member 7b which is formed to be movable in the direction of an arrow in FIG. 1, and the attaching position of the selector diaphragm 7 is determined, so that the aperture of the selector diaphragm 7 coincides with one of through holes formed in the plate member 7b. The size of each through hole of the plate member 7b is set to be sufficiently larger than that of the aperture of the selector diaphragm 7. Another selector diaphragm 7a having a different aperture pattern is attached to another through hole of the plate member 7b. The selector diaphragm 7 is arranged at a position conjugate with the color filter 5 with respect to the objective lens 6, and limits light transmitted through the objective lens 6 by partially shielding an optical image of the color filter 5 formed by the objective lens 6. The light receiving element 8 receives light, passing through the selector diaphragm 7, of light components transmitted through the color filter 5, and outputs an output signal with a voltage value corresponding to the amount of the received light. Therefore, only light components from the optical image of the color filter 5 formed in the aperture of the selector diaphragm 7 are detected by the light receiving element 8. In this manner, the selector diaphragm 7 determines the detection area on the color filter 5 to be detected by the light receiving element 8. The light receiving element 8 comprises a photomultiplier, a photodiode, or the like. The above-mentioned detection means also comprises an observation finder and a finder for confirming the position of the selector diaphragm 7 (neither finders are shown).

Figure 3:
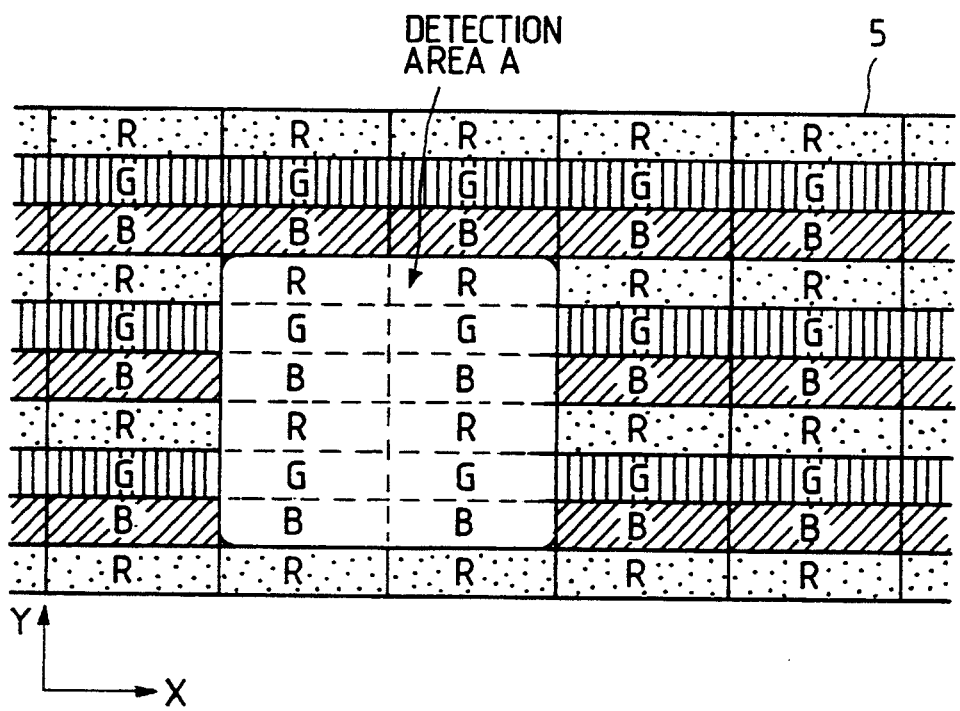
FIG. 3 is a view showing the detection area in the first embodiment.

The detection area of the color filter 5 detected by the light receiving element 8 is determined based on the aperture pattern of the selector diaphragm 7 and the magnification of the objective lens 6. More specifically, as shown in FIG. 3, for example, when a detection area A on the color filter 5 is assumed to be a square area with one side of 660 μm, and the magnification of the objective lens 6 is assumed to be x2, the aperture pattern of the selector diaphragm 7 is formed to be a square with one side of 1,320 μm (=1.32 mm). The illumination area on the color filter 5 by the illumination optical system is set to be substantially equal to or larger than the detection area A on the color filter 5.

Figure 2:
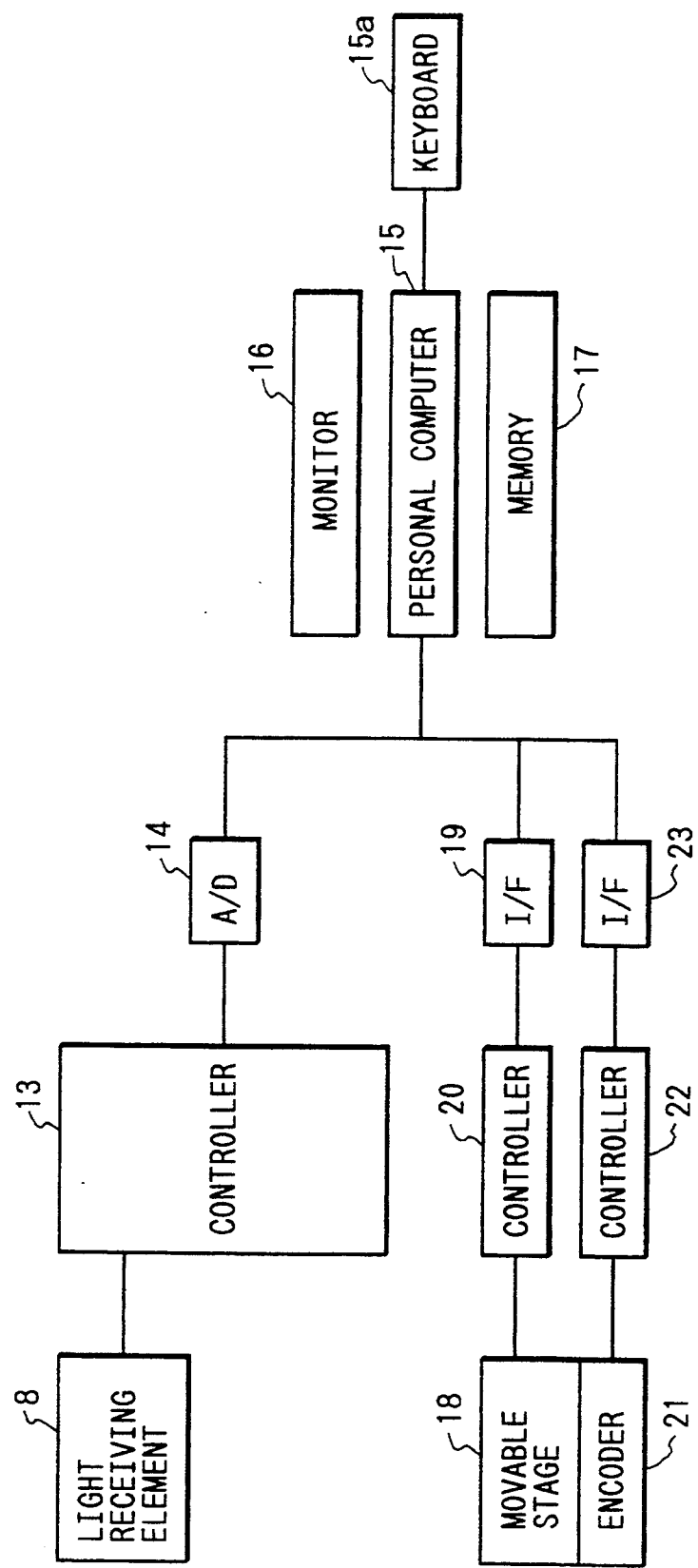
FIG. 2 is a block diagram showing the electrical structure of the first embodiment.

FIG. 2 is a block diagram showing the electrical system of the first embodiment, and shows the arrangement of processing means for executing arithmetic processing of an output signal from the detection means, and the arrangement of driving means for moving the color filter 5 as an object to be inspected, and detecting its moving position in the embodiment shown in FIG. 1.

An output signal from the light receiving element 8 is input to a controller 13. The controller 13 has an amplifier, and amplifies and outputs the output signal. The output signal from the controller 13 is input to an A/D converter 14. The A/D converter 14 converts the input signal into a digital signal, and outputs the digital signal to a personal computer 15. The personal computer 15 calculates the difference between the input digital signal value, i.e., the measurement value indicating the amount of light detected by the light receiving element 8, and a pre-stored reference value. If the calculated difference falls within an allowable range, the personal computer 15 determines that a portion, within the detection area A, on the color filter 5 is good and free of defects; if the calculated difference falls outside the allowable range, the personal computer 15 determines that the portion is defective. When the personal computer 15 determines that the detected portion is defective, it performs classification of defect levels. Note that defect discrimination will be described in detail later in the description of setting of the detection area (to be described later).

The personal computer 15 also performs scanning control of the stage 18. The personal computer 15 outputs a control signal for moving the stage 18. This control signal is input to a controller 20 via an interface 19, and the controller 20 outputs a driving signal for driving the motor attached to the stage 18. The stage 18 is moved in the X and Y directions in accordance with the driving signal. An encoder 21 for detecting the moving amount of the stage 18 is attached to the stage 18. The encoder 21 outputs up-down pulses the number of which is proportional to the moving distance of the stage 18 to a controller 22. The controller 22 outputs the pulses from the encoder 21 to the personal computer 15 via an interface 23. The personal computer 15 outputs a control signal for controlling the movement of the stage 18 on the basis of the signal from the encoder 21.

Figure 6:
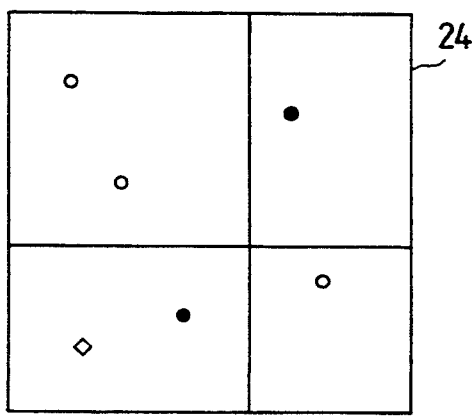
FIG. 6 is a view showing an example of a defect display on a monitor of the first embodiment.

The calculation result of the personal computer 15 is displayed in real time on a monitor 16 together with the position of the stage 18 detected by the encoder 21, and is stored in an external memory 17. The monitor 16 displays the positions and levels of defects in combination, as shown in FIG. 6. Referring to FIG. 6, a frame 24 represents the edge of the color filter 5. An open circle mark represents defect class 1 corresponding to the lowest defect level, a full circle mark represents defect class 2 corresponding to the middle defect level, and an open rhombus mark represents defect class 3 corresponding to the highest defect level. The crossing point of cross lines in the vertical and horizontal directions indicates the current position of the detection area on the color filter 5.

The color filter will be described below with reference to FIGS. 4 and 5, and subsequently, the setting operation of the detection area will be described with reference to FIGS. 3 and 4.

Figure 4:
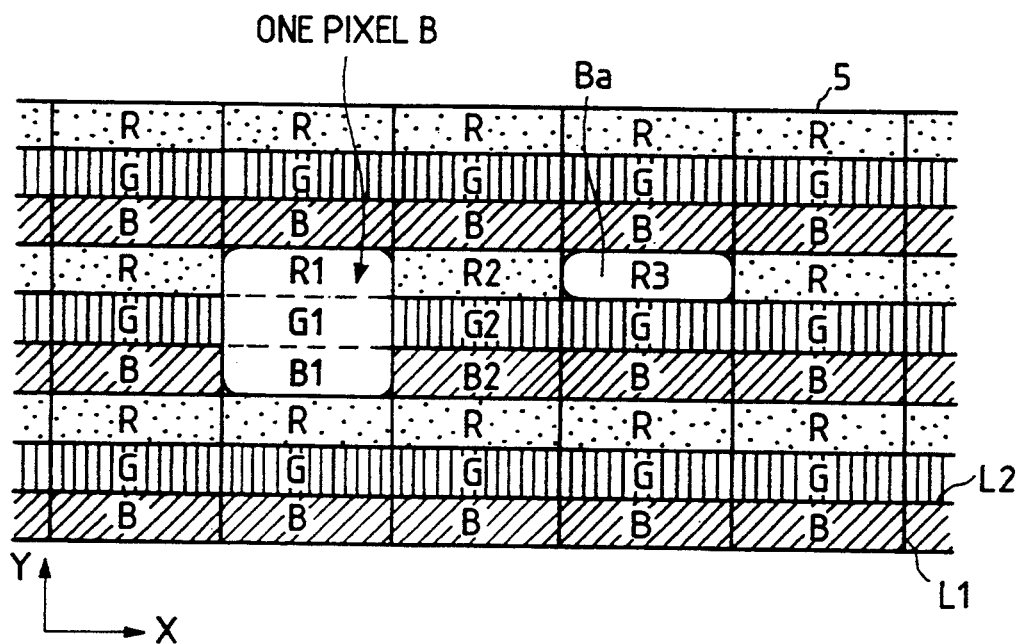
FIG. 4 is a view showing the arrangement of a mesh type color filter.

The color filter 5 shown in FIG. 4 is called a mesh type color filter, and is formed by joining small filter segments R, G, and B having substantially the same shape via vertical and horizontal black lines L1 and L2. The small filter segment R is a red small filter segment, the small filter segment G is a green small filter segment, and the small filter segment B is a blue small filter segment. These small filter segments R, G, and B are repetitively arranged at the same pitch in the Y direction, and the small filter segments of the same color are repetitively arranged at the same pitch in the X direction, thereby forming the color filter 5 as a whole. One pixel of the color filter 5 has a size equal to that of one pixel of a color liquid crystal display which uses the color filter 5. In this embodiment, an area B shown in FIG. 4 corresponds to the size of one pixel. In the area of one pixel, the small filter segments are arranged at a predetermined ratio independently of any one-pixel area positions on the color filter 5.

In this color filter 5, filter segments having the same shape and size and the same color like small filter segments R1 and R2, G1 and G2, and B1 and B2 in FIG. 4 have the same transmittance. Therefore, for example, when the small filter segments R1 and R2 are illuminated with light beams having equal light amounts, they transmit light beams having the same light amount. Also, small filter segments of different colors like the small filter segments R1 and G1, R1 and B1, and G1 and B1 have different transmittances. Therefore, for example, even when the small filter segments R1 and G1 are illuminated with light beams having equal light amounts, they transmit light beams having different light amounts.

Figure 5:
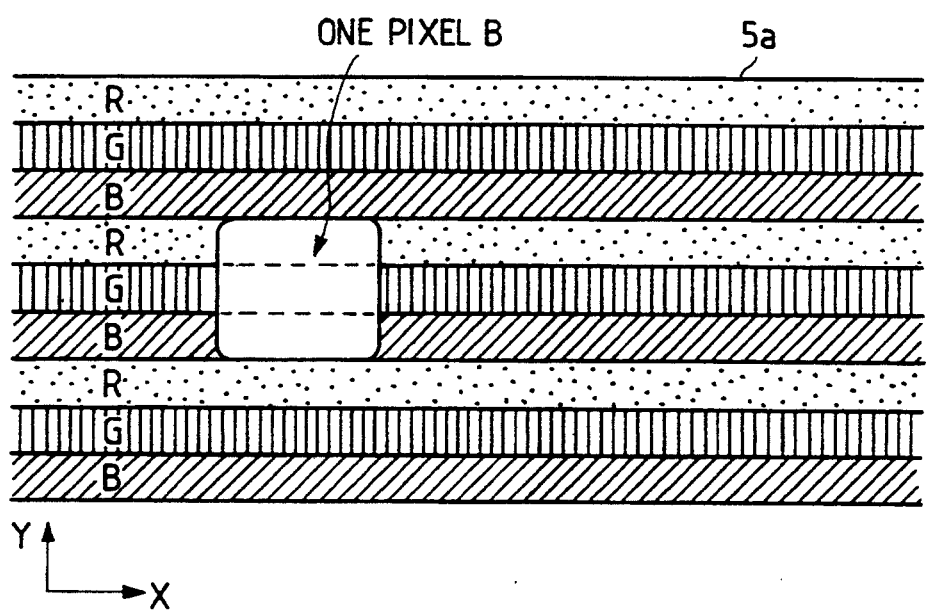
FIG. 5 is a view showing the arrangement of a line type color filter.

FIG. 5 shows a line type color filter 5a. The line type color filter 5a is divided by black lines in the X direction, and line filter segments of respective colors are periodically arranged at the same pitch in the Y direction. In the line type color filter 5a as well, since one pixel is determined by the size of one pixel of the color liquid crystal display, an area B shown in FIG. 5 corresponds to the size of one pixel. In this one pixel area, the line filters of the respective colors can be considered as divided small filter segments. In the case of the line type filter, the transmittances of the small filter segments have the same relationship as that of the small filter segments of the mesh type filter.

The detection area will be described below. As shown in FIG. 4, for example, assume that an area Ba having a size equal to the size of one small filter segment is set to be a detection area. In this case, the amount of light passing through the area Ba when the area Ba is located on a small filter segment R3, as shown in FIG. 4, is different from the amount of light passing through the area Ba when the area Ba is located on a small filter segment of another color, e.g., a segment G1. More specifically, the measurement value of the amount of light passing through the area Ba changes depending on a difference in color of the filter segment even when both the small filter segments R3 and G1 are normal. Of course, when a small filter segment suffers from a defect, the measurement value of the amount of light passing through the area Ba also changes from the measurement value obtained when the segment does not suffer from any defect. Therefore, the inspection apparatus must determine whether the measurement value changes due to a change in color or due to a defect, resulting in difficult defect discrimination.

On the other hand, as shown in FIG. 4, assume that an area B equal to one pixel including one each of the small color segments R1, G1, and B1 of the respective colors is set to be a detection area. The amount of light passing through the area B when the area B is located on the small filter segments R1, G1, and B1 is equal to the amount of light passing through the area B when the area B is moved in the X direction, and is located on the small filter segments R2, G2, and B2. Therefore, when the color filter 5 does not suffer from any defect, the amount of light passing through the area B is substantially constant independently of the position of the area B, which includes the small filter segments of the respective colors at the predetermined ratio, on the color filter 5. The apparatus of the present invention pays attention to this regularity, and sets a predetermined area including small filter segments of respective colors at the predetermined ratio to be the detection area, thereby performing defect discrimination of the color filter.

More specifically, in the apparatus of the first embodiment, as shown in FIG. 3, the detection area A corresponding to the aperture pattern of the selector diaphragm 7 is set to be an area corresponding to four pixels on the color filter 5. The detection area A includes four each of the small filter segments R, G, and B. The apparatus of the first embodiment detects the amount of light passing through the four-pixel area to be a substantially constant measurement value when no defect is present on the color filter 5; it detects the amount of light different from that obtained in a defect-free state when a defect is present on the color filter 5.

The operation of the apparatus of the first embodiment will be described below. Light emitted from the light source 1 illuminates a portion on the color filter 5 via the field stop 2, the aperture stop 3, and the illumination lens 4. The illumination area on the color filter 5 is determined by the aperture pattern of the field stop 2 and the magnification of the illumination lens, and is set to be an area slightly wider than the detection area A. The light radiated onto the color filter 5 is transmitted through the color filter 5, and reaches the objective lens 6. The objective lens 6 focuses the light transmitted through the color filter 5, and forms an optical image of the color filter 5 on the selector diaphragm 7. The selector diaphragm 7 allows only light components, which form the optical image of the color filter 5 on the aperture portion of the selector diaphragm 7, of the light transmitted through the objective lens 6 to pass therethrough. At this time, the area of the optical image on the color filter 5 formed on the aperture portion of the selector diaphragm 7 corresponds to an optical image of the detection area A on the color filter 5 shown in FIG. 3. The light passing through the selector diaphragm 7 reaches the light receiving element 8, and the light receiving element 8 outputs an electrical signal proportional to the amount of the received light. A voltage signal from the light-receiving element 8 is converted into a digital signal via the controller 13 and the A/D converter 14, and the digital signal is output to the personal computer 15.

When the color filter 5 is placed on the stage 18, the personal computer 15 outputs a control signal for moving the stage 18, so that the detection area A is located at the detection start position on the color filter 5. The control signal is input to the controller 20 via the interface 19. The controller 20 generates a driving signal for driving the electric motor of the stage 18 on the basis of the control signal, and drives the motor. The encoder 21 attached to the stage 18 generates pulses according to the moving amount of the stage upon movement of the stage 18. The controller 22 generates a digital signal indicating the moving amount of the stage 18 on the basis of the pulses from the encoder 21, and outputs the generated digital signal to the personal computer 15 via the interface 23. The personal computer 15 calculates the center of the detection area A with respect to the color filter 5, i.e., the position of the optical axis, on the basis of the digital signal from the controller 22. When the detection area A coincides with the detection start position on the color filter 5, the personal computer 15 outputs a control signal for stopping the driving operation of the stage 18 to the controller 20, thus temporarily stopping the stage 18.

The personal computer 15 acquires, from the A/D converter 14, a digital signal indicating the measurement value of the amount of light transmitted through the detection area A after the stage 18 is stopped at the detection start position, e.g., at the upper right corner position on the color filter 5. The personal computer 15 calculates the difference between the acquired digital signal and a pre-stored reference value. When the calculated difference falls within an allowable range, the personal computer 15 determines that the detected portion of the color filter 5 is good; when the difference falls outside the allowable range, it determines that the detected portion is defective. Thereafter, the personal computer 15 outputs a control signal for controlling the stage 18, so that the detection area A is moved at a constant speed over the entire area on the color filter 5. Thus, the personal computer 15 controls the controller 20 to continuously move the stage 18, continuously acquires digital signals from the A/D converter 14 at the same time, and continuously performs defect discrimination using the acquired digital signals. At this time, the personal computer 5 calculates the current position of the detection area A, which is moving on the color filter 5, on the basis of the digital signals from the controller 22, and displays the current position of the detection area A on the monitor 16 using a cross mask, as shown in FIG. 6.

When the personal computer 15 determines in the defect discrimination that the detected portion is defective, it discriminates the defect level. Then, the personal computer 15 stores defect level data and the position of the detection area A in the memory 17, and displays a mark indicating the defect level at the position, corresponding to the position of the detection area A, on the monitor 16, as shown in FIG. 6. The defect level is classified into three classes in accordance with the difference between the digital signal and the reference value.

The types of defects to be detected will be described below. Since the detection area corresponding to four pixels is set, the apparatus of the first embodiment simultaneously receives light in a relatively large area as compared to detection areas (C to K) in other embodiments to be described later. For this reason, the apparatus of the first embodiment can detect a wide-area defect which has a transmittance slightly different from that of a normal filter segment, and is continuously present over a wide range. When a color filter with a defect is used in a color liquid crystal display, a man can notice the defect upon watching the display. A man cannot easily identify a filter segment with a transmittance slightly different from that of a normal segment to be a defect. However, if a defect which has a small transmittance difference from that of a normal filter segment is continuously present in a wide area, a man can identify the filter segments in this area as a defect. Yet, since the wide-area defect has a small transmittance difference from a normal filter segment, it is difficult to detect the defect within a narrow detection area. The apparatus of the first embodiment detects a total for filter segments with small transmittance differences by setting a relatively wide detection area, thereby detecting the wide-area defect. The apparatus of the first embodiment can shorten the detection time of the entire color filter since a large detection area is set.

A plurality of different selector diaphragms are prepared like the stops 7 and 7a in FIG. 1. For example, when the aperture size of the selector diaphragm 7a shown in FIG. 1 is set in correspondence with the detection area B on the color filter 5, i.e., one pixel of the color filter 5, as shown in FIG. 4, the detection area can be changed from a four-pixel area to a one-pixel area by exchanging the selector diaphragms 7 and 7a. In this case, since the amount of light detected by the light receiving element 8 becomes a signal proportional to the light amount corresponding to one pixel, the above-mentioned reference value stored in the computer 15 is changed accordingly. In the apparatus of the first embodiment, the reference value is changed on the basis of an input from a keyboard 15a when the selector diaphragms 7 and 7a are exchanged with each other. Note that exchange between the selector diaphragms 7 and 7a may be automatically detected, and the reference value may be automatically set accordingly.

The apparatus of the first embodiment comprises an observation finder (not shown), and the memory 17 stores the presence/absence, level, and generation position of a defect. Therefore, upon completion of the above-mentioned defect inspection, the color filter 5 may be moved to the defect position stored in the memory 17, and a portion determined to be a defect can be visually observed using the observation finder. The observation filter comprises, e.g., binocular lens barrels with eyepiece lenses of a microscope.

If necessary, a previously inspected color filter may be placed on the stage 18, and data measured in the previous inspection may be read out from the memory 17, so that the apparatus of this embodiment may display a defect map of the previously inspected color filter, or may move the color filter to the defect position discriminated in the previous inspection to observe the defect via a microscope.

Note that the apparatus of the first embodiment performs defect inspection of the mesh type color filter, as shown in FIG. 3, but can similarly inspect the line type color filter.

In addition to the mesh type color filter shown in FIG. 3, a mesh type color filter in which small filter segments of the respective colors are periodically repetitively arranged in the Y direction, and small filter segments of different colors are arranged in the X direction is also available. Also, the mesh type color filter includes a filter in which small filter segments of the respective colors have different sizes in units of colors, and a filter in which each small filter segment has a shape other than a rectangular shape shown in FIG. 3. However, in any type of filters, the size and shape of small filter segments of the same color are substantially constant in a single filter. Therefore, when the detection area is set to be an area corresponding to one pixel of the color filter or an integer multiple of one pixel (an integer is 2 or more) like in this embodiment, the ratio of small filter segments of the respective colors is substantially constant independently of the sizes and shapes of small filter segments in the detection area. Note that the present invention is not limited to an area corresponding to one pixel of a color filter or an integer multiple of one pixel as long as the ratio of small filter segments of the respective colors in the predetermined area is always constant.

Apparatuses of embodiments to be described hereinafter detect a narrow-area defect which has a transmittance relatively largely different from that of a normal filter segment, and is present in a small area.

The apparatus of the second embodiment will be described below with reference to FIG. 8. The apparatus of the second embodiment comprises the same illumination optical system, detection means, and control circuit as those in the apparatus of the first embodiment, except for the aperture pattern of the selector diaphragm, i.e., the detection area. The same reference numerals in the second embodiment denote the same parts as in the first embodiment, and a detailed description thereof will be omitted.

Figure 8:
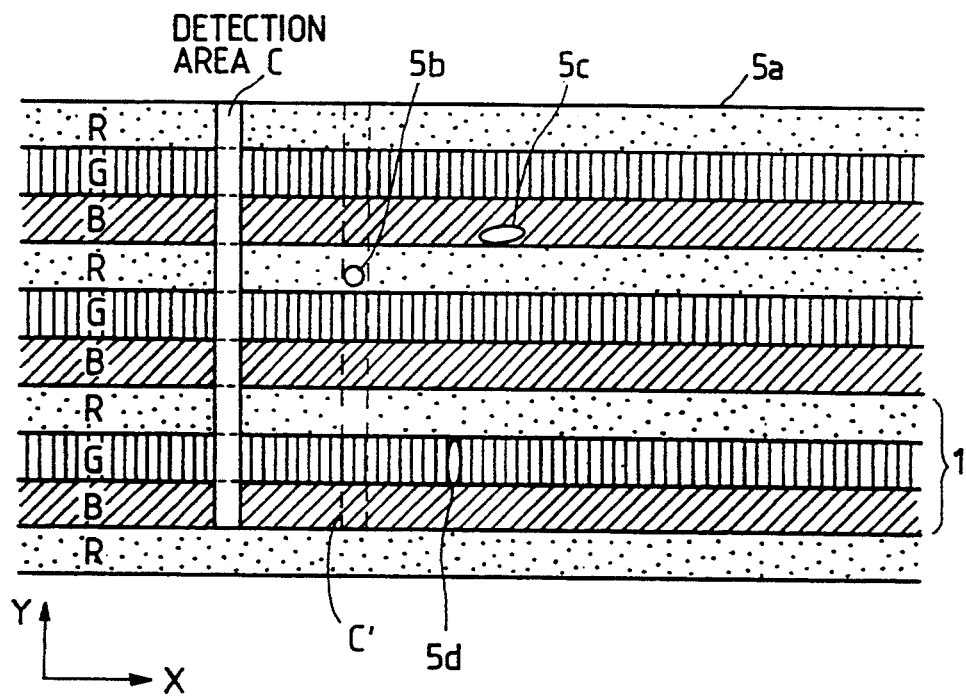
FIG. 8 is a view showing the detection area according to the second embodiment of the present invention.

The apparatus of the second embodiment has a strip-like detection area C elongated in the Y direction, as shown in FIG. 8. More specifically, the detection area C is 20 μm wide in the X direction as large as the size of a defect to be detected, and is 990 μm long in the Y direction in correspondence with the length of three pixels of a color filter. Therefore, the ratio of small filter segments of the respective colors in the detection area C is constant.

The operation of the apparatus of the second embodiment will be described below. The illumination optical system illuminates a color filter 5a. Of light components transmitted through the color filter 5a, light passing through the selector aperture 7 is detected by the light receiving element 8, and the controller 13 and the A/D converter 14 generate a digital signal corresponding to the amount of received light and output the digital signal to the personal computer 15. The personal computer 15 compares the digital signal with a reference value, thereby performing defect discrimination of the color filter. The above-mentioned operation is repetitively performed over the entire color filter 5a by moving the stage 18.

The defect discrimination of the second embodiment will be described below. The defect discrimination of the second embodiment is basically the same as that in the apparatus of the first embodiment. By moving the stage 18, the detection area C is moved from the position, illustrated in FIG. 8, on the color filter 5a in the X direction. At this time, when the detection area C is located on a position C′ including a defect 5b, the amount of received light detected by the light receiving element 8 changes by the defect 5b. For example, when the defect 5b is a hole formed in a filter segment, the transmittance of the portion of the defect 5b increases, and the amount of received light also increases. The personal computer 15 compares the measurement value of the light amount in the detection area C at the position C′ including the defect 5b with a reference value. When the measurement value falls outside an allowable range, the personal computer 15 determines a defect. Upon determination of the defect, the personal computer 15 further performs classification. At this time, although the transmittance of a normal portion is largely different form that of the defect 5b, since the ratio of the defect 5b in the detection area C is small, it is determined that the defect 5b belongs to class 1, and the determined class is stored in the memory 7 together with position data of the stage upon discrimination. At the same time, the detected defect is displayed on the monitor 16 in the form of an open circle mark.

The apparatus of the second embodiment can discriminate and detect the shape of a defect. For example, when a defect 5c elongated in the X direction is detected, the defect discrimination results of class 1 like the defect 5b are continuously detected in the X direction. When a defect 5d elongated in the Y direction is detected, since the ratio of the defect 5d in the detection area C increases, a defect discrimination result of class 2 is obtained.

Figure 7:
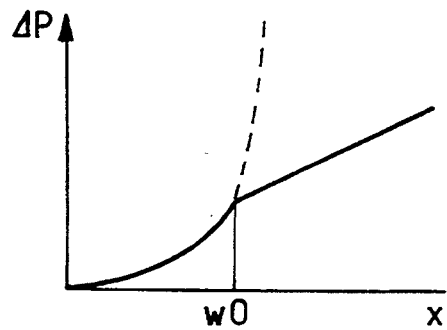
FIG. 7 is a graph showing an example of the relationship between the defect size of a color filter and the change in measurement value.

FIG. 7 shows the relationship between a size x, in the X direction, of a defect and a measurement value ΔP of the amount of received light in an apparatus comprising the elongated detection area like in the second embodiment. In FIG. 7, a solid curve represents the relationship obtained when a width w, in the X direction, of the selector diaphragm is w0, and a broken curve represents the relationship obtained when w>w0. When the length, in the X direction, of the detection area is set to be w0, the measurement value ΔP of the amount of received light changes at a timing when the size x of a defect is w0. Therefore, the length w, in the X direction, of the detection area is preferably set to be equal to the length w0, in the X direction, of a defect to be detected.

In this manner, since the apparatus of the second embodiment has the detection area c with a small length in the X direction, it can detect both a defect as small as the detection area length in the X direction and a defect larger than the small defect, and can detect a defect with high positional resolution especially in the X direction. In the apparatus of the second embodiment, since the detection area C is elongated in the Y direction, the number of times of scanning in the X direction can be decreased, and the time required for detecting defects on the entire color filter can be shortened.

In the apparatus of the second embodiment, the length, in the Y direction, of the detection area is preferably set to be an integer multiple of one pixel so as to obtain a constant amount of light when a color filter does not suffer from any defect.

Figure 9:
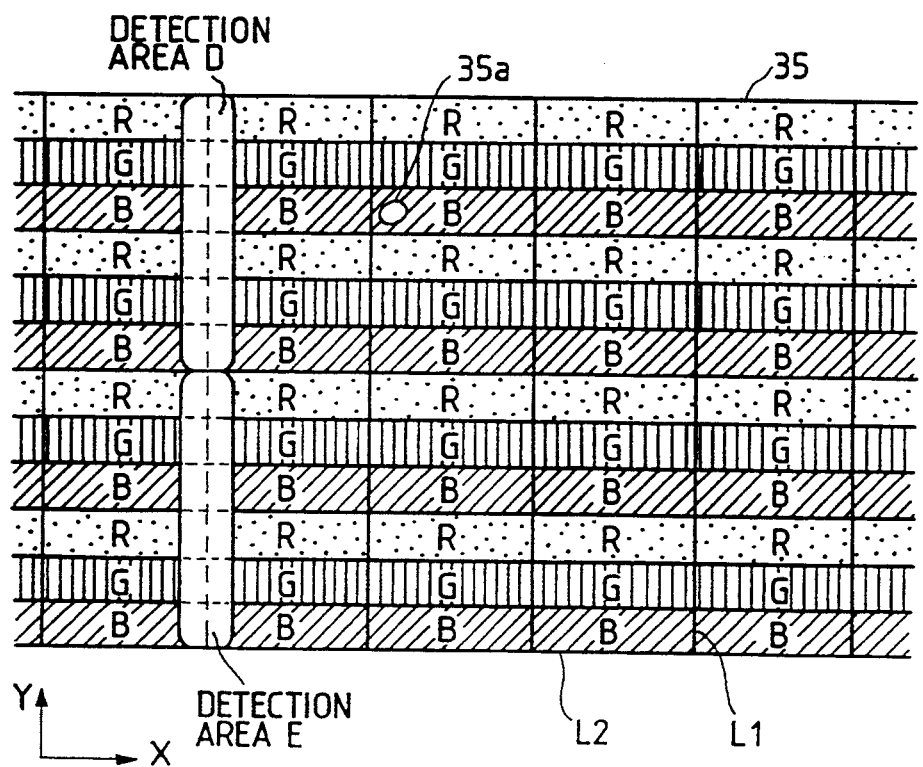
FIG. 9 is a view showing the detection area according to the third embodiment of the present invention.

The apparatus of the third embodiment will be described below with mainly reference to FIGS. 9 to 12C. The apparatus of the third embodiment comprises a plurality of detection areas D and E, as shown in FIG. 9.

Figure 10:
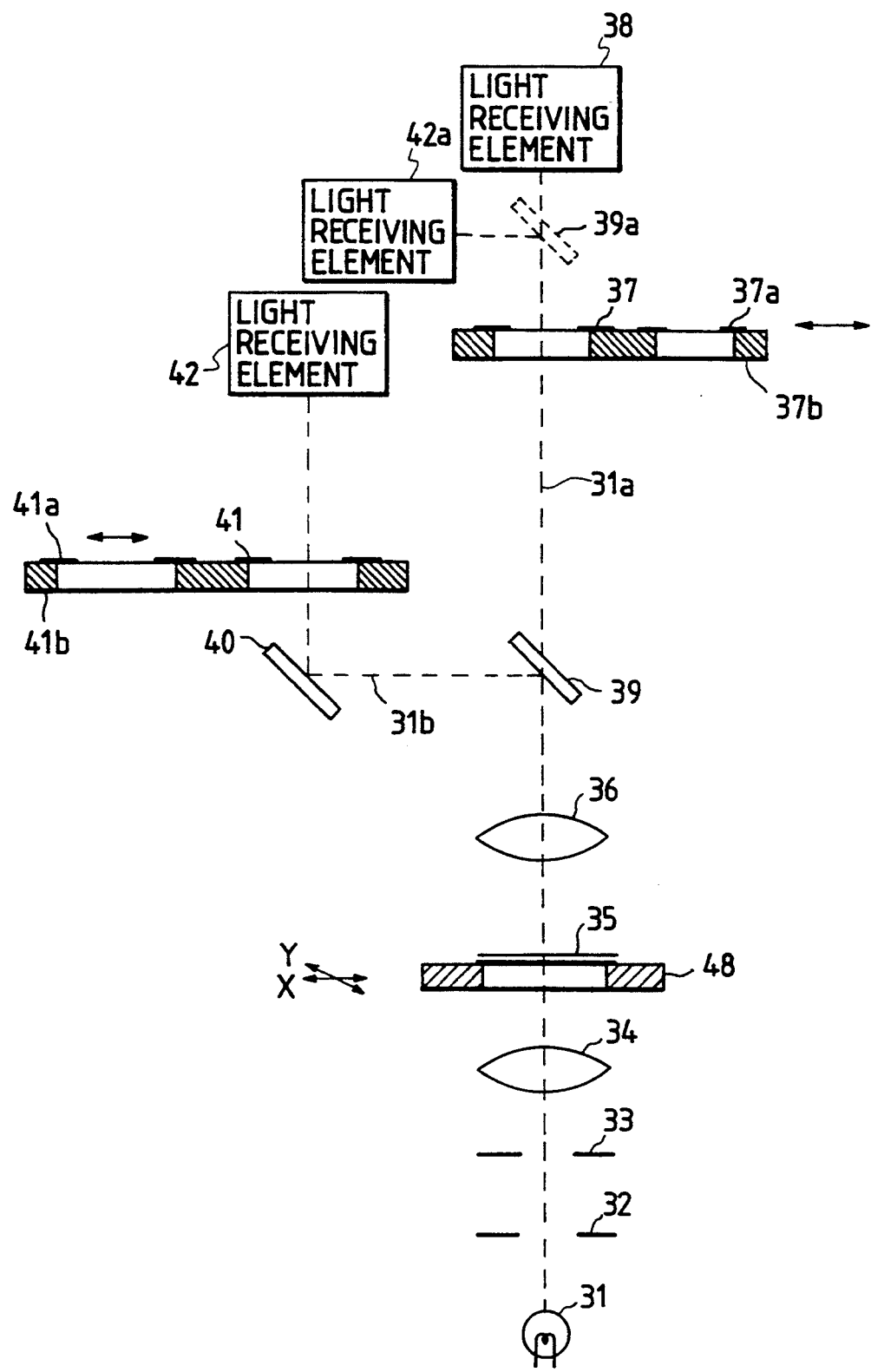
FIG. 10 is a view showing the optical arrangement of the third embodiment.

As shown in FIG. 10, the apparatus of the third embodiment has an illumination optical system comprising a light source 31, a field stop 32, an aperture stop 33, and an illumination lens 34. The illumination optical system is the same as that in the first embodiment although its components are denoted by different reference numerals. A color filter 35 as an object to be inspected is placed on a stage 48 which is movable in the X and Y directions, and the illumination optical system illuminates a predetermined area on the color filter 35. Note that the predetermined area, i.e., an illumination area is determined by the field stop 32, and covers detection areas D and E on the color filter 35.

A detection means will be described below. The detection means is also basically the same as that in the apparatus of the first embodiment. The detection means of the third embodiment is arranged to oppose the illumination optical system with respect to the color filter 35, and detects some light components transmitted through the color filter 35. The detection means comprises an objective lens 36, selector diaphragms 37 and 41, light receiving elements 38 and 42, a half mirror 39, and a total reflection mirror 40. The objective lens 36 forms an optical image of the color filter 35 illuminated by the illumination optical system on the selector diaphragms 37 and 41. The objective lens 36 is exchangeable in the same manner as the objective lens 6 of the first embodiment, and an objective lens with a relatively small magnification is used.

The half mirror 39 is arranged between the objective lens 36 and the selector diaphragm 37, and splits light transmitted through the objective lens 36 into light on the side of an optical axis 31a and light on the side of an optical axis 31b. The light on the side of the optical axis 31a is light transmitted through the half mirror 39. The transmitted light reaches the selector diaphragm 37 arranged on the optical axis 31a, and forms an optical image of the color filter 35 on the selector diaphragm 37. The selector diaphragm 37 has an aperture elongated in the Y direction and corresponding to the detection area D shown in FIG. 9, and allows light components from the optical image formed in the aperture of the selector diaphragm 37 to pass therethrough. The selector diaphragm 37 is attached to a rectangular plate member 37b which is formed to be movable in the direction of an arrow in FIG. 10, as in the apparatus of the first embodiment. The attaching position of the selector diaphragm 37 is determined, so that the aperture of the selector diaphragm 37 coincides with one of through holes of the plate member 37b. Another selector diaphragm 37a having a different aperture pattern is attached to another through hole of the plate member 37b. The light receiving element 38 is arranged behind the selector diaphragm 37. The light receiving element 38 detects light components from the optical image formed in the aperture of the selector diaphragm 37, and outputs an electrical signal corresponding to the amount of received light.

On the other hand, the light on the side of the optical axis 31b is light reflected by the half mirror 39, and is reflected by the total reflection mirror 40 in a direction parallel to the optical axis 31a. The light reflected by the total reflection mirror 40 reaches the selector diaphragm 41. The selector diaphragm 41 has an aperture corresponding to the detection area E shown in FIG. 9. More specifically, the shape and size of the aperture of the selector diaphragm 41 are the same as those of the selector diaphragm 37, and the selector diaphragms 37 and 41 are arranged, so that the detection areas D and E do not overlap each other on the color filter 35. The selector diaphragm 41 is attached to one of through holes of a rectangular plate member 41b in the same manner as the selector diaphragm 37, and is movable in the direction of an arrow in FIG. 10. Note that another selector diaphragm 41a is fixed to another through hole. The selector diaphragm 41 allows light components, from the optical image formed in the aperture of the selector diaphragm 41, of light transmitted through the objective lens 36 to pass therethrough. The light passing through the selector diaphragm 41 is detected by the light receiving element 42, and the light receiving element 42 outputs an electrical signal corresponding to the amount of received light.

Figure 11:
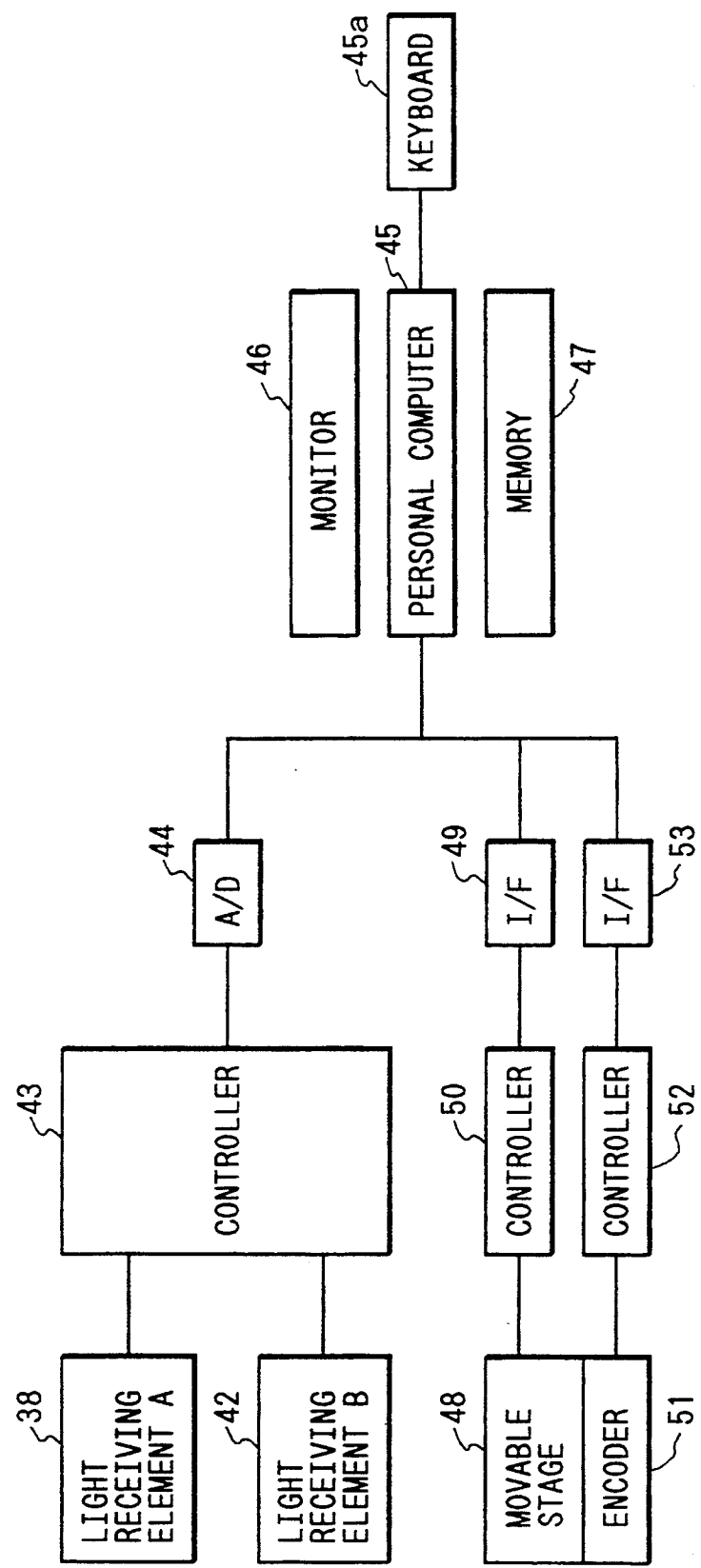
FIG. 11 is a block diagram showing the electrical arrangement of the third embodiment.

FIG. 11 is a block diagram showing the electrical system of the third embodiment. Electrical signals from the two light receiving elements 38 and 42 are converted into digital signals via a controller 43 and an A/D converter 44, and the digital signals are output to a personal computer 45. The personal computer 45 calculates the differences between the two digital signals and a pre-stored reference value. Defect discrimination is attained by discriminating, based on the comparison results, whether or not the measurement values of the light amounts fall within an allowable range. Upon detection of a defect, the detected defect is classified into three classes.

The personal computer 45 also controls an electric motor of the stage 48 via an interface 49 and a controller 50. The personal computer 45 moves the stage 48, so that the color filter 35 moves relative to the detection areas D and E. An encoder 51 is attached to the stage 48, and a pulse signal form the encoder 51 is input to the personal computer 45 via a controller 52 and an interface 53. The personal computer 45 calculates the positions of the detection areas D and E with respect to the color filter 35 in accordance with the pulse signal, and displays the calculated positions on a monitor 46 using a cross mark shown in FIG. 6. When the personal computer 45 discriminates a defect in the defect discrimination, it stores the defect level in a memory 47 together with the position of the stage 48 detected by the encoder 51, and displays it on the monitor 46 at the same time, as shown in FIG. 6.

In the apparatus of the third embodiment, defect discrimination corresponding to each of the detection areas D and E is performed in the same manner as the defect discrimination corresponding to the detection area C in the apparatus of the second embodiment. The apparatus of the third embodiment can measure an area corresponding to a sum of the detection areas D and E by a single scanning operation in the X direction. Therefore, as compared to the apparatus of the second embodiment using a single detection area, the number of times of scanning of the stage 48 in the X direction can be halved, and the time required for detecting defects on the entire color filter can be shortened.

An apparatus as a modification of the apparatus of the third embodiment will be described below. In the apparatus of this modification, a control sequence is improved.

Figure 12A:
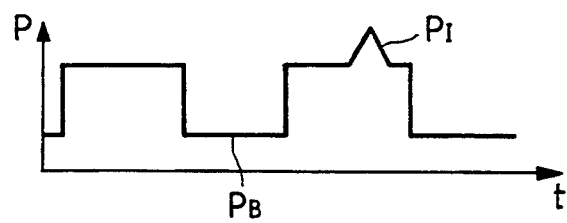
FIGS. 12A to 12C are waveform charts showing the output waveforms from a light receiving element and a controller obtained when the detection area is designated, as shown in FIG. 9.
Figure 12B:
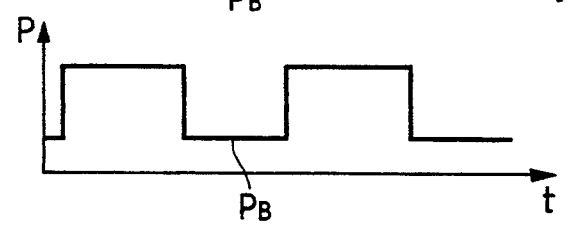

Detection signals in the apparatus of the third embodiment will be explained below. The mesh type color filter 35 has black lines L1 and L2 which partition small filter segments R, G, and B of the respective colors, and respectively extend in the Y and X directions, as shown in FIG. 9. In the apparatus of the third embodiment, the detection areas D and E are set to be elongated in the Y direction. In the apparatus of the third embodiment with these detection areas D and E, a difference in amount of light passing through the detection areas D and E appears in correspondence with the periods of the black lines L1 in the Y direction for partitioning color small filter segments R, G, and B. FIGS. 12A and 12B show the amounts of light received by the light receiving elements 38 and 42. Referring to FIGS. 12A and 12B, a signal $P_B$ represents a bottom state when the detection area D or E passes over a black line L1 of the color filter 35. A difference in amount of received light caused by the black line L1 cannot be ignored as compared to even a defect to be detected. More specifically, as shown in FIG. 12A, when the amount of light detected upon detection of a defect 35a is represented by P1, a difference in amount of light detected upon detection of a defect is smaller than that detected upon passing over a black line L1. The change in light amount caused by a black line is conspicuous in the apparatuses of the second and third embodiments in each of which the width, in the X direction, of the detection area is decreased to detect a small defect.

Thus, in the apparatus according to the modification of the third embodiment, control is made as follows. More specifically, since the detection areas D and E are arranged in the Y direction, the influence of the black lines L1 similarly appears in the two detection areas. Therefore, a difference signal obtained by subtracting the output signal from one light receiving element 42 from the output signal from the other light receiving element 38 is calculated, thereby eliminating the influence of the black lines L1.

The apparatus of this modification has substantially the same arrangement as that shown in FIGS. 9 and 10, except that the controller 43 generates a difference signal indicating the difference between the output signals from the light receiving elements 38 and 42, and the personal computer 45 performs defect discrimination by utilizing this difference signal.

FIG. 12A shows the output waveform of the light receiving element 38 corresponding to the detection area D, and FIG. 12B shows the output waveform of the light receiving element 42 corresponding to the detection area E. Assuming that the defect 35a is present at a point on the color filter 35 corresponding to the detection area D, as shown in FIG. 9, a signal P1 deformed according to the defect 35a is detected in the output signal waveform of the light receiving element 38 corresponding to the detection area D, as shown in FIG. 12A. In contrast to this, no signal deformed by a defect is detected from the output signal waveform of the light receiving element 42 corresponding to the detection area E in which the defect 35a is not present, as shown in FIG. 12B. Note that the same bottom signal $P_B$ is generated by a black line L1 in the two light receiving element 38 and 42.

Figure 12C:
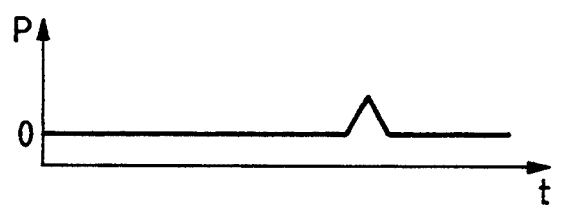

The controller 43 amplifies the output signal waveforms from the two light receiving elements 38 and 42, and generates a difference signal obtained by subtracting the signal from the light receiving element 42 from the signal from the light receiving element 38. FIG. 12C shows the difference signal, which clearly represents only a deformed portion corresponding to the defect 35a. The difference signal output from the controller 43 is converted into a digital signal, and the digital signal is compared with a reference value by the personal computer 45. The personal computer 45 compares the difference signal and the reference value, and when the computer 45 determines that the difference signal falls outside an allowable range, it determines a defect. Thereafter, the personal computer classifies the detected defect. The discrimination result of the personal computer 45 is stored in the memory 47, and is displayed on the monitor 46 in real time, as described above.

The apparatus of this modification can eliminate a change in light amount caused by the black lines by using a difference signal.

Note that the apparatus according to the modification of the third embodiment can also inspect a line type color filter.

The fourth embodiment will be described below with reference to FIGS. 13A to 13C, FIGS. 14 and 15, and FIGS. 16A to 16C.

First, the apparatus of the third embodiment associated with the apparatus of the fourth embodiment will be additionally described. In the apparatus of the third embodiment, when the detection areas D and E aligned in the Y direction are slightly shifted from each other in the X direction, defect discrimination cannot be normally performed.

Figure 13A:
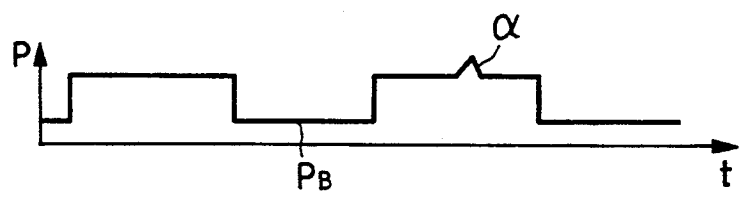
FIGS. 13A to 13C are waveform charts showing the output waveforms from the light receiving element and the controller obtained when the detection area is designated, as shown in FIG. 9, and detection areas A and B are slightly shifted from each other.
Figure 13B:
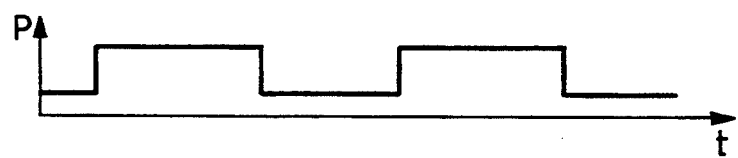
Figure 13C:
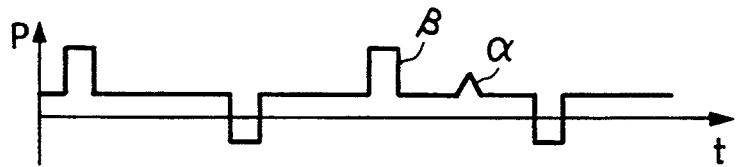

When the detection areas D and E are arranged to be shifted in the X direction in the apparatus of the third embodiment, the output waveforms from the light receiving elements 38 and 42 are respectively as shown in FIGS. 13A and 13B. When the controller 43 generates a difference signal indicating the difference between these two signals, the difference signal has a noise component $\beta$ in addition to a defect $\alpha$, as shown in FIG. 13C. The personal computer 45 recognizes the noise component $\beta$ as a defect upon calculation of the difference between the difference signal and the reference value. Therefore, in the apparatus of the third embodiment, the detection areas D and E must be arranged so as not to be shifted from each other in the X direction. However, it is troublesome to mechanically precisely align the detection areas D and E.

The direct cause of the above-mentioned erroneous detection is generation of the noise component $\beta$ due to a positional shift, in the X direction, between the detection areas D and E, and the erroneous detection is also caused by the fact that the noise component $\beta$ is abruptly generated and assumes a large value. More specifically, if the noise component $\beta$ is a negligible signal as compared to the defect $\alpha$ even when it is generated, no problem is posed. In the apparatus of the fourth embodiment, the noise component $\beta$ is eliminated.

Figure 14:
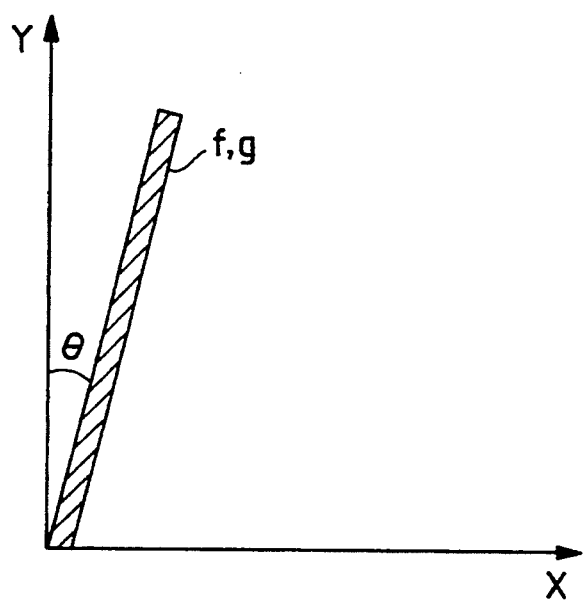
FIG. 14 is a view showing an example of the pattern of a selector diaphragm.
Figure 15:
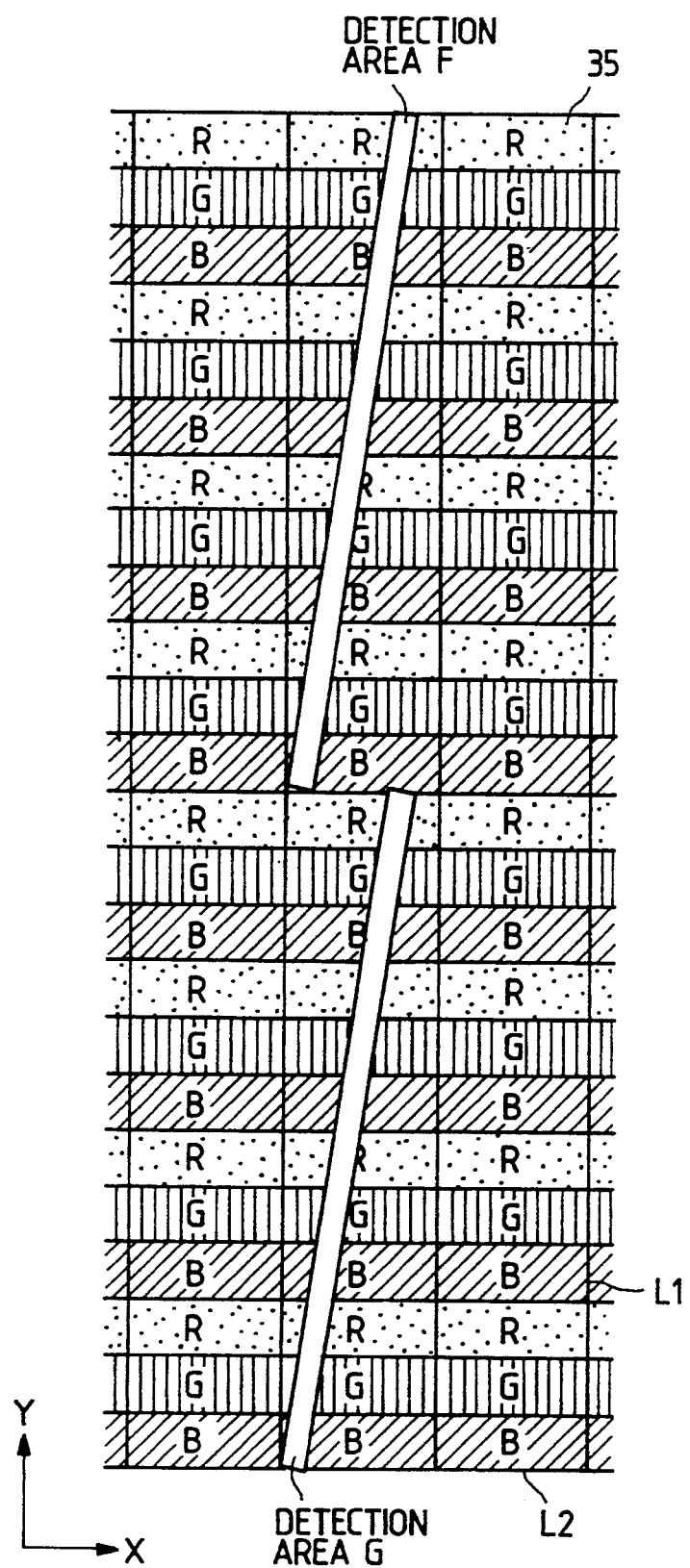
FIG. 15 is a view showing an example of the method of designating the detection area of a mesh type color filter using the selector diaphragm shown in FIG. 14.
Figure 16A:
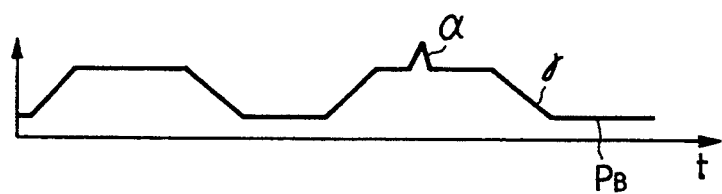
FIGS. 16A to 16C are waveform charts showing the output waveforms from the light receiving element and the controller obtained when the detection area is designated, as shown in FIG. 15, and detection areas A and B are slightly shifted from each other.
Figure 16B:
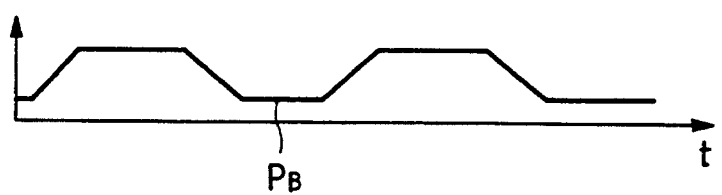

The apparatus of the fourth embodiment has basically the same arrangement as the apparatus of the third embodiment, except for the shapes of detection areas. Note that the same reference numerals in the fourth embodiment denote the same parts as in the third embodiment, and a detailed description thereof will be omitted. An aperture pattern f or g of the selector diaphragm in the apparatus of the fourth embodiment is formed into a strip shape elongated substantially in the Y direction, as shown in FIG. 14, and is arranged so that its longitudinal direction is inclined at 5° ($\theta = 5°$) from the Y direction. FIG. 15 shows detection areas F and G on the color filter 35 defined by the selector diaphragms of the fourth embodiment. As shown in FIG. 15, the detection areas F and G are aligned in the Y direction. Each of the detection areas F and G has a width, in the X direction, of 20 μm, and is formed into a strip shape elongated in the Y direction. The longitudinal direction of each detection area is arranged to be slightly inclined from the Y direction. In this case, the output signal waveforms from the light receiving elements 38 and 42 corresponding to the detection areas F and G are respectively as shown in FIGS. 16A and 16B. Referring to FIGS. 16A and 16B, a signal $\alpha$ represents a defect, and a signal $\gamma$ and a bottom signal $P_B$ represent states wherein the amounts of light received by the light receiving elements 38 and 42 are changed by a black line L1. More specifically, when the detection areas G and Y are arranged to be inclined from the Y direction, the ratio of a black line L1 on the color filter 35, which line is located within the detection area F or G, gradually increases, or gradually decreases. Therefore, of the output signals from the light receiving elements 38 and 42, a portion changed by a black line L1, in particular, the signal $\gamma$, changes slowly.

Figure 16C:
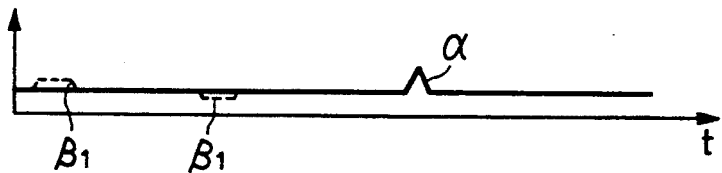

FIG. 16C shows a difference signal indicating the difference between the output signals from the light receiving elements 38 and 42. More specifically, the clear noise component $\beta$ shown in FIG. 13C does not appear in the difference signal even when the detection areas F and G are slightly shifted from each other in the X direction. If the detection areas F and G are arranged to be shifted from each other in the X direction on the color filter 35 so as to cause a change in signal level, a noise component with a low signal level appears like a signal $\beta 1$ indicated by a dotted curve. However, in this case, the signal level of the signal $\beta 1$ representing the noise component can be minimized as compared to the apparatus of the third embodiment. Therefore, in the apparatus of the fourth embodiment, the noise component $\beta 1$ can be ignored even if it is generated.

In the fourth embodiment as well, the detection area length in the Y direction is set to be as large as 1,320 μm (for four pixels) as in the second and third embodiments, and the time required for detecting defects on the entire color filter can be shortened.

The apparatus of the fifth embodiment will be described below with reference to FIGS. 17 and 18, FIGS. 19A to 19C, and FIGS. 20A to 20C. The apparatus of the fifth embodiment is basically the same as the apparatus of the fourth embodiment, except that the aperture pattern of the selector diaphragm is further improved. Note that the same reference numerals in the fifth embodiment denote the same parts as in the fourth embodiment, and a detailed description thereof will be omitted.

The apparatus of the fifth embodiment has the same illumination optical system and detection means shown in FIG. 10 and the same control means shown in FIG. 11 as those in the apparatus of the third embodiment, except for the aperture patterns of the selector diaphragms 37 and 41. Therefore, the illumination optical system illuminates an area including detection areas H and I shown in FIG. 18. The light receiving element 38 receives light in the detection area H, which light has passed through the selector diaphragm 37, and the light receiving element 42 receives light in the detection area I, which light has passed through the selector diaphragm 41. The controller 43 generates a difference signal indicating the difference between the output signals from the light receiving elements 38 and 42, and the personal computer 45 compares the difference signal and a reference value to perform defect discrimination. Thereafter, the personal computer 45 classifies the detected defect into three classes. The personal computer 45 displays the discrimination result on the monitor 46 together with the position data of the detection areas H and I and the defect class, and stores them in the memory 47.

Figure 17:
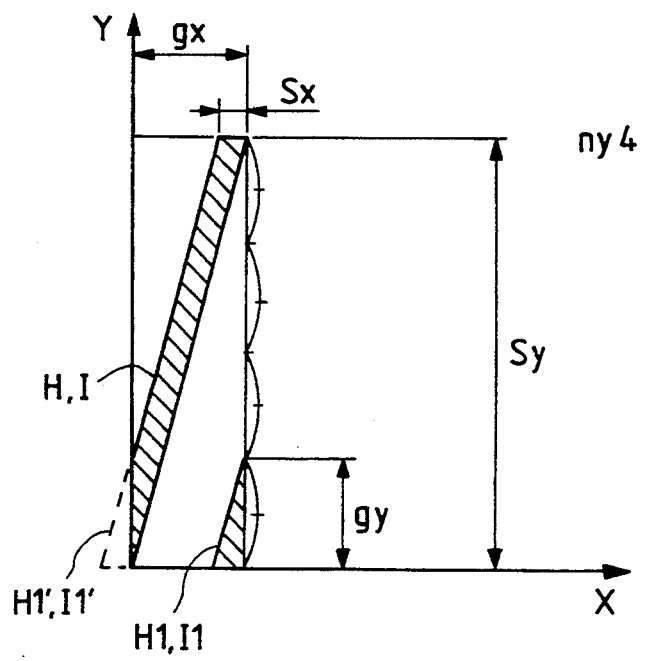
FIG. 17 is a view showing another example of the pattern of the selector diaphragm.

The detection areas H and I will be described below. As shown in FIG. 17, each of the detection areas H and I of the apparatus of the fifth embodiment has a small width Sx in the X direction, and is elongated in the Y direction. The longitudinal direction of each detection area is inclined with respect to the Y direction, and the area of each of the detection areas H and I is set to be equal to that of one pixel on the color filter. The detection areas H and I also include areas H1 and I1, respectively. These areas H1 and I1 correspond to portions H1' and I1' indicated by a dotted line in FIG. 17, and are re-positioned to fall within a range of areas gx and gy.

The setting operation of the detection areas H and I will be described below. Assume that the length, in the X direction, of one pixel is represented by gx, the length, in the Y direction, of one pixel is represented by gy, the number of pixels, in the Y direction, of the selector diaphragm is represented by ny (in the fifth embodiment ny=4), the length, in the X direction, of the selector diaphragm (37, 41) is represented by sx, and the length, in the Y direction of the selector diaphragm is represented by sy. If these parameters are set to satisfy:

$$sx = gx + ny$$

$$sy = gy \times ny$$

then, the areas of the detection areas H and I satisfy:

$$sx \times sy = gx \times gy$$

When this relationship is satisfied, each of the detection areas H and I corresponds to an area for one pixel of the color filter 35.

Note that the areas of the detection areas H and I may satisfy the following relationship so that each of the detection area has an area corresponding to an integer multiple (n times) of one pixel:

$$sx \times sy = n \times gx \times gy$$

Note that the detailed dimensions of the detection areas H and I are determined as follows based on the above-mentioned equation. For example, when a defect of 30 μm or more is to be detected on a color filter in which one pixel is defined by 330 μm×330 μm, ny=10, sx=33 μm, and sy=3300 μm.

FIG. 18 shows the arrangement of the detection areas H and I of the apparatus of the fifth embodiment. In the apparatus of the fifth embodiment, the detection areas H and I which are set, as described above, are aligned in the Y direction.

Figure 19A:
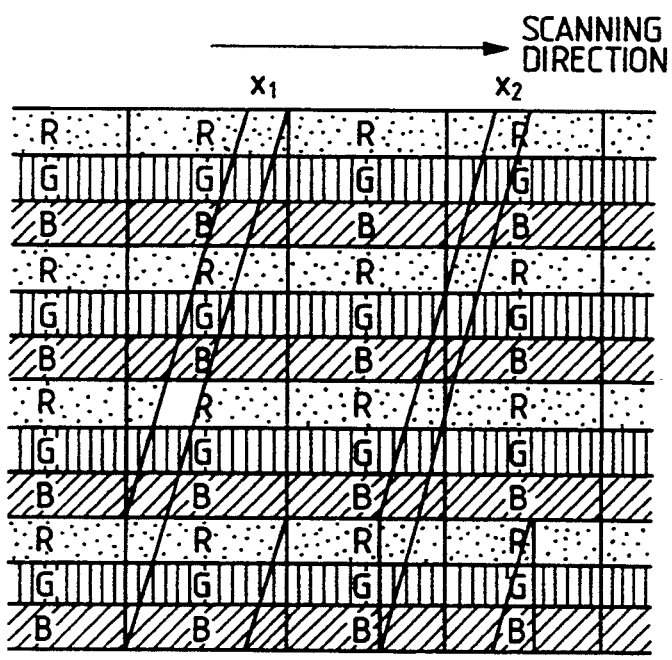
FIGS. 19A to 19C are views showing that the amount of light passing through the selector diaphragm is equal to that for one pixel of the mesh type color filter when the detection area is designated, as shown in FIG. 18.
Figure 19B:
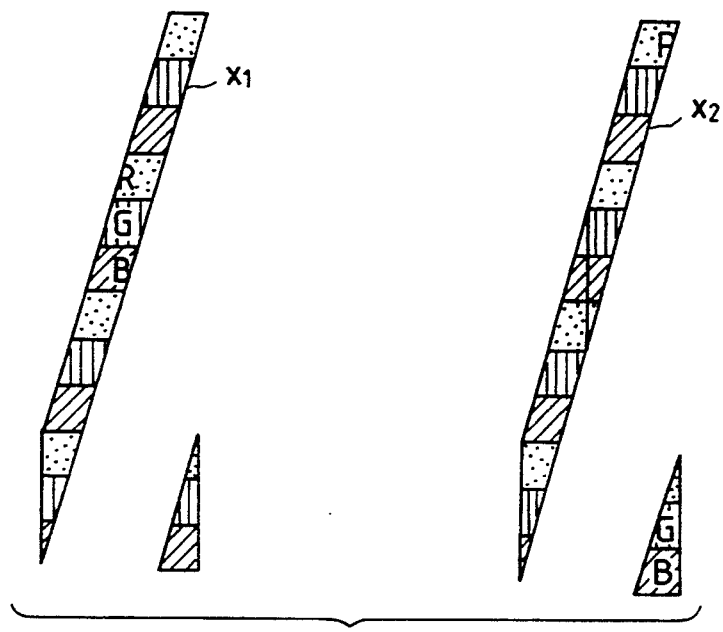
Figure 19C:
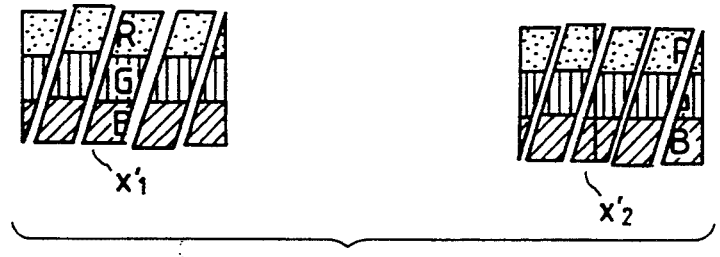

The detection areas H and I of the apparatus of the fifth embodiment always include one pixel of the color filter 35 independently of the position on the color filter 35. More specifically, the detection areas H and I are moved relative to the color filter 35. At this time, for example, assume that one detection area H is moved from a position x1 to a position x2, as shown in FIG. 19A. In this case, the patterns of the color filter 35 which can be observed from the positions x1 and x2 of the detection area H are as shown in FIG. 19B. When these patterns x1 and x2 are cut and pasted, they can be modified, as shown in FIG. 19C. Each of the patterns x1 and x2 shown in FIG. 19C at the two positions of the detection area H corresponds to an area for one pixel as in the pixel area B shown in FIG. 4.

The waveforms of the output signals from the light receiving elements 38 and 42 will be described below. FIGS. 20A to 20C show the output waveforms of signals from the light receiving elements 38 and 42 in the apparatus of the fifth embodiment. The detection areas H and I always correspond to areas for one pixel of the color filter 35, and a one-pixel area includes small filter segments R, G, and B of the respective colors at a predetermined ratio and also includes a black line at a predetermined ratio. Therefore, the output signal waveform from the light receiving element 38 corresponding to the detection area H has a constant output level, as shown in FIG. 20A, when the color filter 35 does not suffer from any defect. Only when a defect is detected, a change $a$ in level corresponding to the defect portion appears in the output signal waveform. Also, the output signal waveform from the light receiving element 42 corresponding to the detection area I has a constant output level, as shown in FIG. 20B, when the color filter 35 does not suffer from any defect. When a difference signal indicating the difference between the output signals from the two light receiving elements 38 and 42 is generated when a defect $a$ is present in the detection area H, only the change $a$ in level indicating the defect can be detected, as shown in FIG. 20C.

In this manner, the apparatus of the fifth embodiment receives light passing through areas which always include one pixel like the detection areas H and I, and performs defect discrimination.

When each of the detection areas H and I is set to be equal to the area of one pixel of the color filter, light passing through an area for one pixel including a black line portion can be detected independently of the positions of the detection areas H and I on the color filter, as has already been described in the first embodiment. Therefore, in the apparatus of the fifth embodiment, the amount of light passing through each of the detection areas H and I is always equal to the amount of light passing through an area for one pixel, and a constant amount of light can always be detected. Therefore, in the apparatus of the fifth embodiment, even when the detection areas H and I are arranged to be shifted from each other in the X direction, light in a one-pixel area can always be detected, and a noise component $\beta$ can be prevented from being generated unlike in the third and fourth embodiments. For this reason, in the apparatus of the fifth embodiment, processing can be remarkably simplified upon execution of a comparison calculation with the reference value in defect discrimination.

In addition, in the apparatus of the fifth embodiment, even when the ratio of the small filter segments R, G, and B of the respective colors in one pixel is not 1:1:1, since light in a one-pixel area is always detected, as shown in FIG. 19A, the light amount in a one-pixel area can be detected at any position on the color filter. Therefore, the apparatus of the fifth embodiment does not depend on the shapes of small filter segments of the respective colors in one pixel. More specifically, even when a small filter segment of each color has a shape other than a rectangle, e.g., a substantially rectangular shape with round corners, the amount of light passing through an area for one pixel is constant. Also, the area for one pixel includes a predetermined black line portion, and the influence of the black line can also be eliminated.

FIG. 21 shows a detection area J as a modification of the detection areas H and I in FIG. 17. The detection area J is also formed to have an area equal to that of one pixel of the color filter 35.

In this modification as well, two detection areas J and K are aligned in the Y direction, and the difference between output signals from the light receiving elements 38 and 42 for detecting light passing through the two detection areas J and K is detected, thereby detecting the presence/absence of a small defect.

Figure 22A:
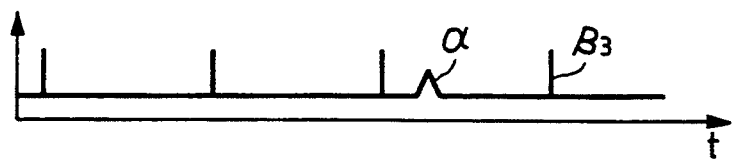
FIGS. 22A to 22C are waveform charts for comparing the output waveforms from the controller respectively obtained when the detection areas are designated, as shown in FIGS. 9, 15, and 18, and when detection areas A and B are slightly shifted from each other.
Figure 22B:
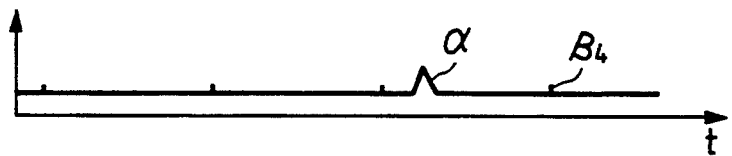
Figure 22C:
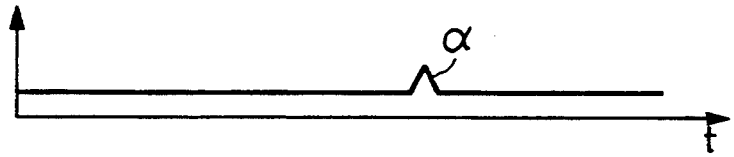

Signal waveforms of the above embodiments (third to fifth embodiments) will be compared with reference to FIGS. 22A to 22C. FIG. 22A shows the difference signal of the apparatus of the third embodiment, FIG. 22B shows the difference signal of the apparatus of the fourth embodiment, and FIG. 22C shows the difference signal of the apparatus of the fifth embodiment. FIGS. 22A to 22C corresponding to these embodiments show the output signal waveforms obtained when the positions between the detection areas D, F, and H and the detection areas E, G, and I are relatively slightly shifted from each other in the X direction. Note that the detection areas are shifted by the same shift amount in the X direction in FIGS. 22A to 22C.

Upon comparison of these output waveforms, a noise component $\beta 3$ of the apparatus of the third embodiment shown in FIG. 22A is maximum, and a noise component $\Gamma 4$ is also generated slightly in the apparatus of the fourth embodiment. In the apparatus of the fifth embodiment, no noise component is detected. That is, the apparatus of the fifth embodiment has the highest S/N ratio.

As can be seen from the above comparison result, when an automatic defect inspection apparatus for a color filter, which apparatus has a plurality of detection areas, is used for detecting a small defect, each detection area is preferably inclined with respect to the Y direction, and the area of each detection area is set to be equal to that of a unit pixel of the color filter or that corresponding to an integer multiple of the unit pixel.

As described above, the present invention pays attention to the regularity, i.e., the fact that the color filter is constituted by repetitively arranging unit pixels. For the sake of simplicity, in the drawings illustrating the above embodiments, a small filter segment of each color has a rectangular shape, and a small black line portion. However, in an actual color filter, each color filter segment may have a shape with at least one round corner in terms of an electrode for driving a liquid crystal of a liquid crystal display although it basically has a rectangular shape. In each of the above embodiments, the black lines L1 and L2 are illustrated by thin lines. However, as can be understood from the signal waveforms shown in FIGS. 12A and 12B, the black lines are often relatively thick lines as compared to small filter segments of the respective colors. The present invention can also cope with a color filter having small color filter segments with round corners and thick black lines.

In the description of the above embodiments, the apparatus of the first embodiment, and the apparatuses of other embodiment embodiments detect different types of defects. More specifically, a wide-area defect which has a low defect level but is generated over a wide area is detected by the apparatus of the first embodiment, and a defect which is relatively small and has a high defect level is detected by the apparatuses of other embodiments. However, the above embodiments have basically the same arrangement, except for the number of detection areas (one or a plurality of detection areas) and the pattern of the selector diaphragm in each embodiment, i.e., the pattern and size of the detection area. Therefore, if the apparatus of the present invention has the arrangement as in the apparatus of the third embodiment shown in FIGS. 10 and 11, it can detect many types of defects by only exchanging selector diaphragms. In the apparatus of the third embodiment, a single detection area can be easily attained by prohibiting processing of an output signal from the light receiving element 42. In the apparatus of the present invention, a plurality of selector diaphragms having different detection areas are prepared in correspondence with the size of one pixel of each color filter, and are exchanged in correspondence with the type of color filter. In this manner, the present invention can be applied to color filters with different pixel sizes.

As a modification of the apparatus of the third embodiment and the subsequent embodiments, the following arrangement may be adopted to perform the same inspection as that in the apparatus having a plurality of detection areas.

The apparatus of this modification has only one detection area. In this apparatus, a color filter is moved relative to the detection area to scan the entire color filter, and measurement values of light amounts at respective positions on the color filter are stored. Upon completion of scanning of the entire color filter, the personal computer 45 compares two arbitrary measurement values of those in units of coordinate positions like comparison between the measurement values of the detection areas D and E in the third embodiment. More specifically, the measurement value of the light amount obtained when the detection area is located at the position x1 in FIG. 19A is compared with the measurement value of the light amount obtained when the detection area is located at the position x2. From this comparison result, the presence/absence, level, and position of a defect are calculated. In this modification, the measurement values at positions shifted in the X direction are compared with each other. Of course, the measurement values at positions shifted in the Y direction may be compared with each other.

In the apparatus of this modification, the half mirror 39, the total reflection mirror 40, the selector diaphragm 41, the light receiving element 42, and a processing circuit for the light receiving element 42 in the controller 43 can be omitted as compared to the apparatuses of the third to fifth embodiments. In this case, since only one detection area is used, the inspection time is longer than those in the third to fifth embodiment, and real-time display is difficult to achieve. The personal computer is required to have a large memory area, and much calculation time for defect discrimination is required. For these reasons, the load on the personal computer increases.

In the apparatus of the present invention, when a plurality of detection areas are arranged, the plurality of detection areas may be arranged at positions shifted in the Y direction like in the third and subsequent embodiments, or may be arranged at positions shifted in the X direction.

In the apparatus of the third embodiment shown in FIG. 10, the optical axis 31b is reflected in a direction parallel to the optical axis 31a using the total reflection mirror 40. In the apparatus of this embodiment, however, the total reflection mirror may be omitted. In this case, the selector diaphragm 41 and the light receiving element 42 are arranged on the extending line of the optical axis 31b transverse to the optical axis 31a.

Each of the apparatuses of the third to fifth embodiments has a half mirror, and light components passing through different detection areas are incident on different light receiving elements using the half mirror. Alternatively, two apertures may be formed on a single selector diaphragm. In this case, in order to guide light components passing through the two apertures on the single selector diaphragm to become incident on different light receiving elements, one of the following methods is required. In the first method, the two apertures are formed in a plane transverse to the optical axis to be positionally separated from each other. In the second method, as indicated by a dotted line in FIG. 10, a reflection element (e.g., a half mirror 39a) for splitting an optical path is arranged between the selector diaphragm 37 and the light receiving element 38, and two light receiving elements 38 and 42a are arranged on optical paths split by the reflection element. Then, the half mirror 39, the total reflection mirror 40, and the aperture stop 41 can be omitted.

In each of the apparatuses of the above embodiments, the selector diaphragm is arranged between the color filter and the light receiving element. However, the present invention is not limited to this, and the selector diaphragm may be arranged between the light source and the color filter. In this case, the selector diaphragm also serves as a field stop, and is arranged at the position of the field stop 2 or 32 shown in FIG. 1 or 10. In this case, the selector diaphragm is used for setting a detection area by illuminating only the detection area on the color filter. Therefore, another selector diaphragm at the position of the selector diaphragm 7 in FIG. 1 or at the position of the selector diaphragms 37 and 41 in FIG. 10 may be omitted. In this case, since light on a relatively outer portion in the detection area may be refracted by the color filter in a direction falling outside the detection area, the measurement value changes depending on the thickness of the color filter itself. Therefore, this arrangement is suitable for a color filter having a small thickness in the optical axis direction.

In the apparatus of the present invention, the selector diaphragms are exchanged using the plate member, but may exchanged by other methods as long as the aperture patterns of the selector diaphragms can be changed. For example, a stop which can deform the aperture pattern may be used. It is preferable that a position adjustment function for finely adjusting the position of the selector diaphragm in a plane transverse to the optical axis be arranged.

The apparatus of the first embodiment may also comprise a plurality of detection areas having the same shape, and detect the difference between signals from the plurality of detection areas, as has been described in the third and subsequent embodiments, thus allowing defect detection strong against noise.

What is claimed is:

1. An automatic defect inspection apparatus for a color filter having a structure in which red, green, and blue areas are continuously, periodically, and repetitively arranged along a predetermined direction, comprising:

light source means for radiating light toward said color filter;

detection means for detecting light radiated from said light source means and transmitted through a predetermined area of said color filter, said predetermined area being set, so that areas of the red, blue, and green areas of said color filter are substantially equal to each other;

limiting means, arranged between said light source means and said detection means to determine said predetermined area of said color filter, for shielding some light components from said light source means; and processing means for performing arithmetic processing of an output signal from said detection means.

2. An apparatus according to claim 1, further comprising:

relative movement means for moving said color filter relative to said predetermined area in a direction transverse to an optical axis, so that said predetermined area is moved on said color filter.

3. An apparatus according to claim 2, further comprising:

a stage for holding said color filter to be movable in the direction transverse to the optical axis, and wherein said relative movement means comprises means for driving said stage so as to move said color filter relative to said predetermined area.

4. An apparatus according to claim 1, wherein said light source means comprises a light source, and an illumination lens for radiating light emitted from said light source toward said color filter, and said limiting means comprises a diaphragm arranged at a position conjugate with said color filter with respect to said illumination lens, and said diaphragm determines said predetermined area by limiting some light components from said light source.

5. An apparatus according to claim 1, further comprising:
an objective lens for guiding the light transmitted through said color filter to said detection means, and
wherein said limiting means comprises a diaphragm arranged at a position conjugate with said color filter with respect to said objective lens, and said diaphragm determines said predetermined area by limiting some light components from said light source.

6. An apparatus according to claim 1, wherein said limiting means comprises a plurality of diaphragms having different aperture patterns, and said plurality of diaphragms are exchangeably arranged between said light source means and said detection means.

7. An apparatus according to claim 1, wherein said color filter is a color filter for a color liquid crystal display, and said predetermined area corresponds to an area on said color filter which area is substantially equal to one pixel of said color liquid crystal display, or an area which is substantially an integer multiple of the one pixel.

8. An apparatus according to claim 7, wherein a length, in the predetermined direction, of said predetermined area corresponds to an integer multiple of a repetitive period of the red, green, and blue areas.

9. An automatic defect inspection apparatus for a color filter having a structure in which red, green, and blue areas are continuously, periodically, and repetitively arranged along a predetermined direction, comprising:
light source means for radiating light toward said color filter;
first detection means for detecting light radiated from said light source means and transmitted through a first area on said color filter;
second detection means for detecting light radiated from said light source means and transmitted through a second area on said color filter, said first and second areas having the same shape;
first limiting means, arranged between said light source means and said first detection means to determine said first area of said color filter, for shielding some light components from said light source means;
second limiting means, arranged between said light source means and said second detection means to determine said second area of said color filter, for shielding some light components from said light source means; and
processing means for executing arithmetic processing of output signals from said first and second detection means, said processing means calculating a difference between signals from said first and second detection means.

10. An apparatus according to claim 9, further comprising:
moving means for moving said color filter relative to said first and second areas in a direction transverse to an optical axis, so that said first and second areas are moved on said color filter.

11. An apparatus according to claim 10, further comprising:
an objective lens for guiding the light transmitted through said color filter toward said first and second detection means, and
wherein said first and second limiting means respectively comprise first and second diaphragms which are arranged at positions conjugate with said color filter with respect to said objective lens, and said first and second diaphragms respectively determine said first and second areas by limiting some light components transmitted through said color filter.

12. An apparatus according to claim 11, wherein apertures of said first and second diaphragms are serially arranged in a direction transverse to the moving direction of said moving means.

13. An apparatus according to claim 11, wherein apertures of said first and second diaphragms are formed to be elongated in a direction transverse to the moving direction of said moving means.

14. An apparatus according to claim 13, wherein a length, in a direction parallel to the predetermined direction of said color filter, of each of said first and second areas corresponds to an integer multiple of a repetitive period of the red, green, and blue areas.

15. An apparatus according to claim 11, wherein a width, in the moving direction of said moving means, of each of said first and second areas substantially corresponds to a size of a defect to be detected.

16. An apparatus according to claim 11, wherein said color filter is a color filter for a color liquid crystal device, and
each of said first and second areas corresponds to an area on said color filter which is substantially equal to an area of one pixel of said color liquid crystal display, or an area which is substantially an integer multiple of the one pixel.

17. An apparatus according to claim 11, wherein said first and second areas are inclined with respect to the moving direction of said moving means.

* * * * *